(12) United States Patent
Katkam et al.

(10) Patent No.: US 9,216,943 B2
(45) Date of Patent: Dec. 22, 2015

(54) PREPARATION OF FINGOLIMOD AND ITS SALTS

(75) Inventors: Srinivas Katkam, Hyderabad (IN); Rajeswar Reddy Sagyam, Hyderabad (IN); Raghavendar Rao Morthala, Medak (IN); Babu Ireni, Hyderabad (IN); Krishna Vinigari, Mahabubnagar (IN); Suresh Kumar Ramdoss, Ramanathapuram (IN); Srinivasulu Rangineni, Mahabubnagar (IN); Arjunkumar Tummala, Visakhapatnam (IN); Javed Iqbal, Hyderabad (IN); Srinivas Oruganti, Hyderabad (IN); Bhaskar Kandagatla, Hyderabad (IN)

(73) Assignee: DR. REDDY'S LABORATORIES LTD., Hyderabad (IN)

( * ) Notice: Subject to any disclaimer, the term of this patent is extended or adjusted under 35 U.S.C. 154(b) by 0 days.

(21) Appl. No.: 14/114,305

(22) PCT Filed: Apr. 27, 2012

(86) PCT No.: PCT/IB2012/000922
§ 371 (c)(1),
(2), (4) Date: Apr. 18, 2014

(87) PCT Pub. No.: WO2012/146980
PCT Pub. Date: Nov. 1, 2012

(65) Prior Publication Data
US 2014/0235895 A1    Aug. 21, 2014

Related U.S. Application Data

(60) Provisional application No. 61/497,228, filed on Jun. 15, 2011, provisional application No. 61/499,957, filed on Jun. 22, 2011, provisional application No. 61/527,742, filed on Aug. 26, 2011, provisional application No. 61/595,189, filed on Feb. 6, 2012.

(30) Foreign Application Priority Data

| Apr. 29, 2011 | (IN) | ............................ 1502/CHE/2011 |
| May 9, 2011 | (IN) | ............................ 1597/CHE/2011 |
| Jul. 13, 2011 | (IN) | ............................ 2401/CHE/2011 |
| Dec. 22, 2011 | (IN) | ............................ 4524/CHE/2011 |

(51) Int. Cl.
| C07C 205/45 | (2006.01) |
| C07C 201/10 | (2006.01) |
| C07C 201/12 | (2006.01) |
| C07C 213/02 | (2006.01) |
| C07C 215/28 | (2006.01) |
| C07C 213/00 | (2006.01) |
| C07C 213/10 | (2006.01) |

(52) U.S. Cl.
CPC ............. *C07C 205/45* (2013.01); *C07C 201/10* (2013.01); *C07C 201/12* (2013.01); *C07C 213/00* (2013.01); *C07C 213/02* (2013.01); *C07C 213/10* (2013.01); *C07C 215/28* (2013.01)

(58) Field of Classification Search
CPC .. C07C 205/45; C07C 213/00; C07C 201/10; C07C 215/28
See application file for complete search history.

(56) References Cited

U.S. PATENT DOCUMENTS

| 5,604,229 A | 2/1997 | Fujita et al. |
| 6,284,915 B2 | 9/2001 | Hirase et al. |
| 6,605,744 B2 | 8/2003 | Abel et al. |
| 8,530,522 B2 | 9/2013 | Jordine et al. |
| 2011/0015425 A1 | 1/2011 | Sedelmeier |
| 2012/0184617 A1 | 7/2012 | Gidwani et al. |

FOREIGN PATENT DOCUMENTS

| CN | 1483721 A | 3/2004 |
| CN | 1528738 A | 9/2004 |
| CN | 1765872 A | 5/2006 |
| CN | 1814583 A | 8/2006 |
| JP | 4079505 B2 | 4/2008 |
| WO | WO 2012041405 A1 * | 4/2012 |

OTHER PUBLICATIONS

International Search Report and Written Opinion dated Oct. 18, 2012, for corresponding International Patent Application No. PCT/IB2012/000922.

Kalita et al., "Synthesis of 2-Nitroalcohols by Regioselective Ring Opening of Epoxides with MgSO4/MeOH/NaNO2 System: A Short Synthesis of Immunosuppresive Agent FTY-720", LETTER, Synlett, 2001, pp. 1411-1414, Issue No. 9, Thieme Stuttgart, New York.

* cited by examiner

*Primary Examiner* — Sudhakar Katakam
(74) *Attorney, Agent, or Firm* — Pergament Gilman & Cepeda LLP; Milagros A. Cepeda; Edward D. Pergament

(57) ABSTRACT

The present application provide processes for the preparation of fingolimod and its pharmaceutically acceptable salts, process for the purification of fingolimod hydrochloride and process for the preparation of amorphous fingolimod hydrochloride.

14 Claims, 4 Drawing Sheets

PREPARATION OF FINGOLIMOD AND ITS SALTS

This application is a National Stage Application under 35 U.S.C. §371 of PCT International Application No. PCT/IB2012/000922 filed Apr. 27, 2012, which claims the benefit of Indian provisional application Nos. 1502/CHE/2011 filed on Apr. 29, 2011; 1597/CHE/2011 filed on May 9, 2011; 2401/CHE/2011 filed on Jul. 13, 2011; 4524/CHE/2011 filed on Dec. 22, 2011 and U.S. Provisional Application Nos. 61/497,228, filed Jun. 15, 2011; 61/499,957, filed Jun. 22, 2011; 61/527,742, filed Aug. 26, 2011 and 61/595,189, filed Feb. 6, 2012, all of which are hereby incorporated by reference in their entireties.

INTRODUCTION

Aspects of the present application provide processes for the preparation of fingolimod and its pharmaceutically acceptable salts, process for the purification of fingolimod hydrochloride and process for the preparation of amorphous fingolimod hydrochloride.

The drug compound known as "fingolimod hydrochloride" has chemical names 2-amino-2-[2-(4-octylphenyl)ethyl]propan-1,3-diol hydrochloride; or 2-amino-2-[2-(4-octylphenyl)ethyl]-1,3-propandiol hydrochloride. It has the structure of formula (I).

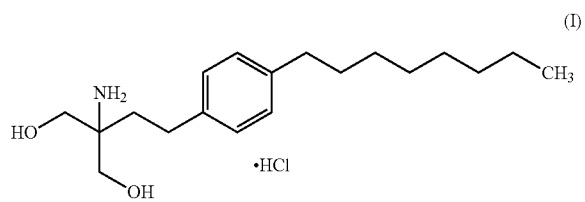 [SMILES: CCCCCCCCc1ccc(CCC(N)(CO)CO)cc1 ; Cl]

Fingolimod hydrochloride is a sphingosine 1-phosphate receptor modulator and is the active ingredient in a product sold by Novartis as GILENYA® in the form of hard gelatin capsules for oral use, for the treatment of patients with relapsing forms of multiple sclerosis.

U.S. Pat. No. 5,604,229, describes a process for the preparation of fingolimod hydrochloride performed by a nine step sequence starting from 2-(4-octanoyl phenyl)ethyl acetate and the crucial reaction step includes the condensation of 2-(4-octylphenyl)ethyl iodide with diethylacetamidomalonate in the presence of sodium ethoxide base and ethanol, and a subsequent reduction with lithium aluminium hydride to obtain 2-acetamido-2-[2-(4-octylphenyl)ethyl]1,3-propanediol, which is acylated in the presence of acetic anhydride and pyridine to give 1,3-propanediyl-2-acetamido-2-[2-(4-octylphenyl)ethyl]ylidene diacetate, followed by hydrolysis using lithium hydroxide to obtain fingolimod. Further, it discloses the use of sodium hydroxide, sodium methoxide, potassium hydride, butyl lithium, triethylamine, diisopropylethylamine, and 1,8-diazabicyclo[5.4.0]undeca-7-ene as bases in the condensation step.

U.S. Pat. No. 6,284,915 discloses a process for the preparation of fingolimod hydrochloride which involves reacting 4'(2-iodoethyl)octanophenone with diethyl acetamido malonate, in the presence of sodium hydride, to give diethyl acetamide-2-(4-octanoyl phenyl)ethyl malonate, which is further reacted with sodium borohydride in methanol, followed by acetylation using acetic anhydride and pyridine, to obtain 1-(4-(3-acetamide-4-acetoxy-3-acetoxymethyl)butylphenyl)octyl acetate, which is hydrolyzed using 1N sodium hydroxide and methanol to give fingolimod.

U.S. Pat. No. 6,605,744 discloses a process for the preparation of fingolimod hydrochloride which involves reacting diethyl acetamido-2-[4-octylphenyl)-2-oxomethylmalonate with sodium borohydride in methanol followed by acetylation using acetic anhydride/pyridine to give 2-acetamido-4-acetoxy-2-acetoxymethyl-4-(4-octylphenyl)butyl acetate which is hydrolyzed to obtain 2-acetamido-2-[2-hydroxy-2-(4-octylphenyl)ethyl]propane-1,3-diol, which is further subjected to reduction in the presence of 5% Pd/carbon in ethanol, followed by treatment with 1N hydrochloric acid in ethanol to give fingolimod hydrochloride.

International Application Publication No. WO 20091115534 A1 discloses processes for the preparation of intermediates useful in the preparation of fingolimod or its salts.

Chinese Patent Application Publication No. 1765872 discloses a process for the preparation of fingolimod hydrochloride, which involves the reaction steps as depicted in Scheme 1 below.

Scheme 1

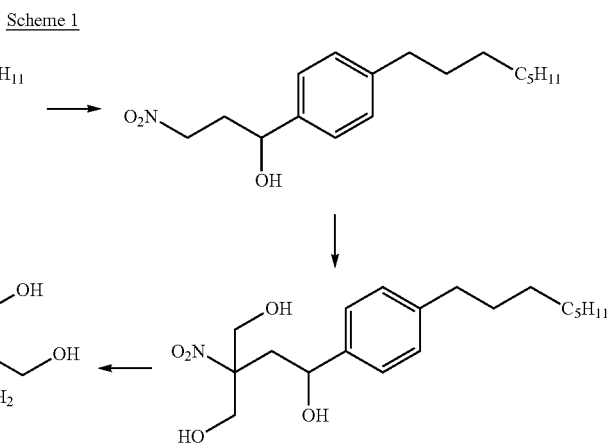

Chinese Patent Application Publication Nos. 1528738, 1483721, and 1814583, and Japanese Patent Publication No. 4079505 also disclose various processes for the preparation of fingolimod hydrochloride and related intermediates.

An article by B. Kalita et al., "Synthesis of 2-Nitroalcohols by Regioselective Ring Opening of Epoxides with MgSO$_4$/MeOH/NaNO$_2$ System: A Short Synthesis of Immunosuppressive Agent FTY-720," *Synlett* 2001, No. 9, pages 1411-1414, discloses a process for the preparation of fingolimod which involves the reaction steps depicted in Scheme 2 below.

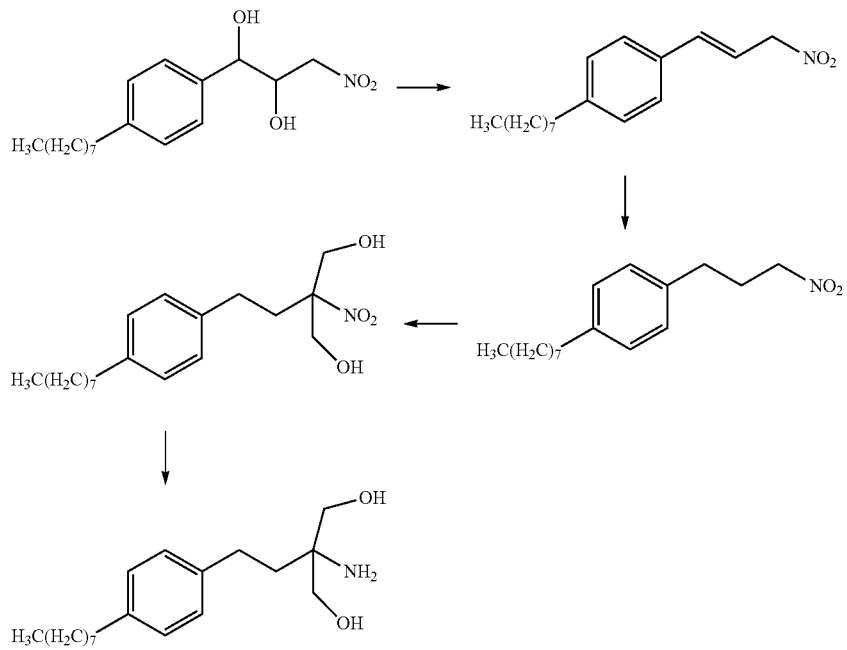

International Application Publication No. WO 2010/055028 A2 discloses crystalline forms of fingolimod hydrochloride salt which are designated as Forms I, II, III, and IV. The publication also discloses a crystalline fingolimod hydrochloride salt, wherein the salt is substantially in the form of a hydrate.

International Application Publication No. WO 2011/009634 A2 discloses pure polymorphic form B and a mixture of polymorphic forms A and B of fingolimod hydrochloride, characterized by X-ray diffraction and differential scanning calorimetry. The publication also discloses processes for the preparation of polymorphic forms, wherein one of the processes for the preparation of polymorphic form B involves dissolving fingolimod hydrochloride in water and subjecting the solution to freeze-drying.

Despite the existence of various processes for the preparation of fingolimod or its salts, there remains a need for improved processes for the preparation of fingolimod and its salts, producing high yields and purity, and being well-suited for use on an industrial scale.

Further, there also remains a need for additional polymorphic forms of fingolimod hydrochloride, and processes for making them.

SUMMARY

In an aspect, the present application provides a process for the preparation of fingolimod or its salt, embodiments comprising:

a) reducing octanophenone of formula (II):

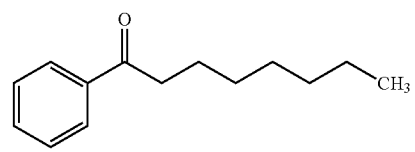

(II)

using a Lewis acid and a trialkyl silane to obtain octylbenzene of formula (III);

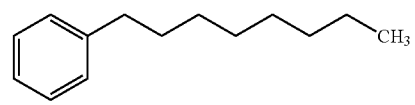

(III)

b) reacting the compound of formula (III) with a 3-halo-propionyl halide to obtain a compound of formula (IV):

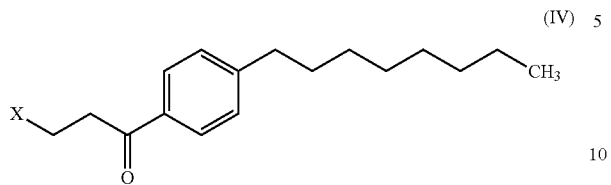

wherein X is a halogen;

c) reacting the compound of formula (IV) with a compound of formula (V):

$$M^{+n}(NO_2)_n \quad (V)$$

wherein M is a metal ion and n is 1, 2, or 3 to obtain a compound of formula (VI); and

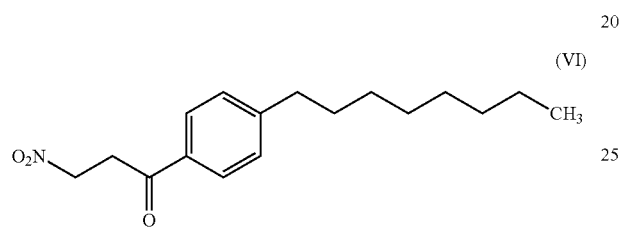

d) converting the compound of formula (VI) to fingolimod of formula (Ia):

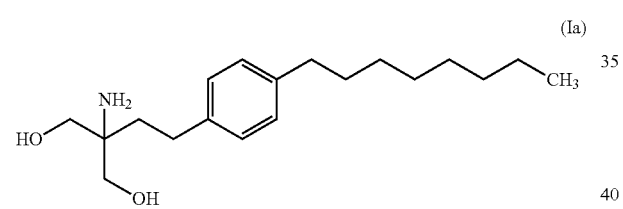

or its salt.

In an aspect, the present application provides a process for the preparation of fingolimod or its salt comprising:

a) reducing 3-nitro-1-(4-octylphenyl)propan-1-one of formula (VI):

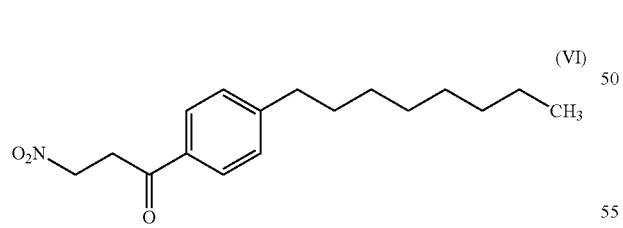

using a Lewis acid and a trialkyl silane to obtain a compound of formula (VII); and

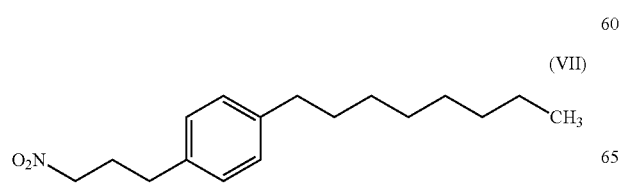

b) converting the compound of formula (VII) to finaolimod of formula (Ia):

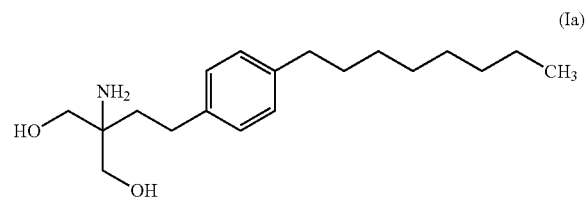 [SMILES: CCCCCCCCc1ccc(CCC(N)(CO)CO)cc1]

or its salt.

In an aspect, the present application provides processes for the preparation of fingolimod or its salt, embodiments comprising:

a) reacting the compound of formula (IX),

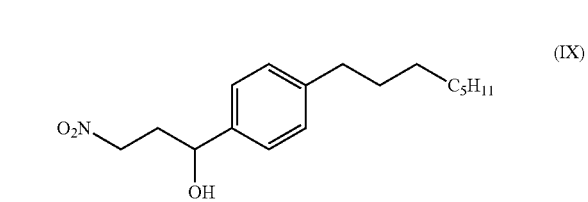

with a reducing agent, to obtain the compound of formula (VII); and

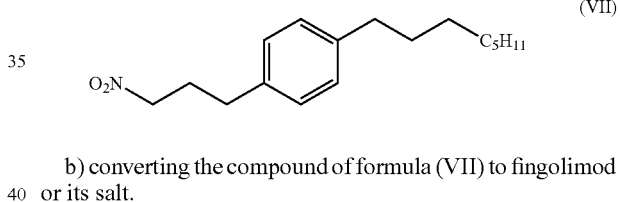

b) converting the compound of formula (VII) to fingolimod or its salt.

In an aspect, the present application provides processes for the preparation of fingolimod or its salt, embodiments comprising:

a) reacting the compound of formula (VII),

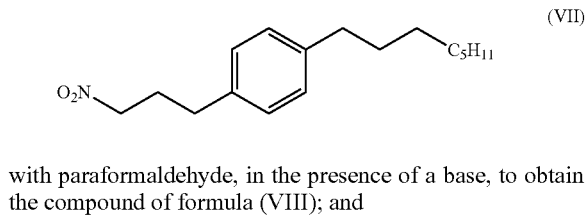

with paraformaldehyde, in the presence of a base, to obtain the compound of formula (VIII); and

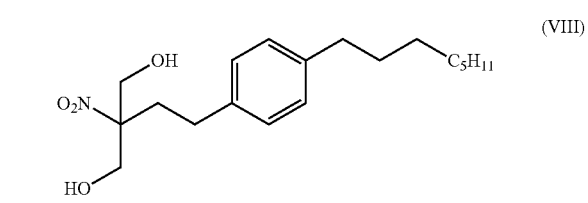

b) converting the compound of formula (VIII) to fingolimod or its salt.

In an aspect, the present application provides processes for the preparation of fingolimod or its salt, embodiments comprising:

a) reacting a compound of formula (X),

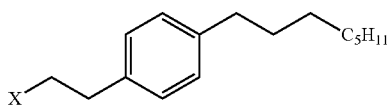
(X)

wherein X is a leaving group, with a compound of formula (XI),

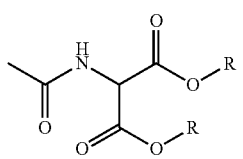
(XI)

wherein R is a $C_1$-$C_4$ alkyl group, in the presence of a metal carbonate, to give a compound of formula (XII);

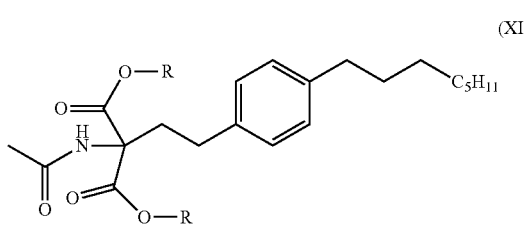
(XII)

b) reacting the compound of formula (XII) with a reducing agent to provide the compound of formula (XIII); and

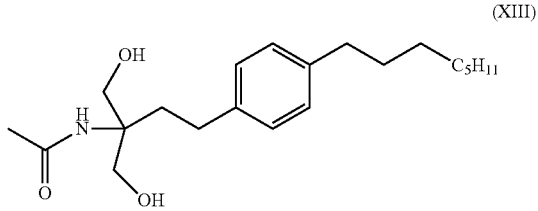
(XIII)

c) converting the compound of formula (XIII) to fingolimod or its salt.

In an aspect the present application provides process for the purification of fingolimod hydrochloride comprising:

(a) providing a solution of fingolimod hydrochloride in methanol or methanol and ethylacetate mixture;

(b) optionally adding ethylacetate;

(c) cooling the solution to a temperature below 10° C.;

(d) isolating fingolimod hydrochloride.

In an aspect, the present application provides an amorphous fingolimod hydrochloride.

In an aspect, the present application provides processes for the preparation of amorphous fingolimod hydrochloride, embodiments comprising:

a) providing a solution of fingolimod hydrochloride and a pharmaceutically acceptable carrier in a solvent; and b) obtaining amorphous fingolimod hydrochloride.

In an aspect, the present application provides pharmaceutical compositions comprising amorphous fingolimod hydrochloride, together with one or more pharmaceutically acceptable excipients.

DETAILED DESCRIPTION

Figure 1:
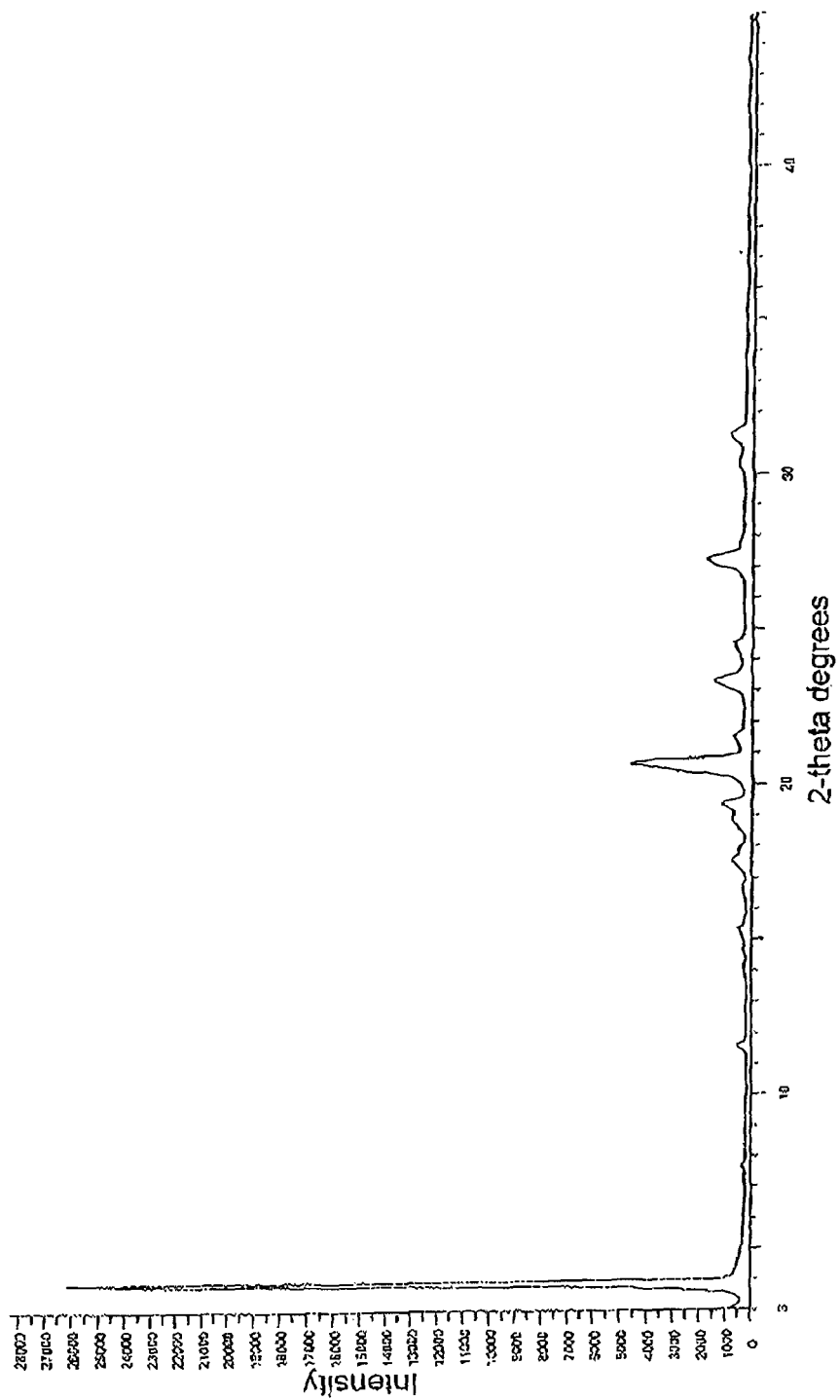
FIG. 1 is an illustration of a powder X-ray diffraction (PXRD) pattern of fingolimod freebase, prepared according to Example 10.

In an aspect, the present application provides a process for the preparation of fingolimod or its salt, embodiments comprising:

a) reducing octanophenone of formula (II):

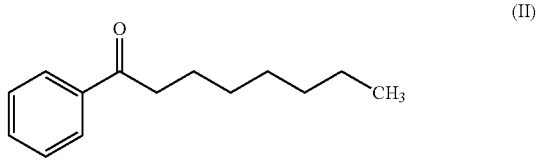
(II)

using a Lewis acid and a trialkyl silane to obtain octylbenzene of formula (III);

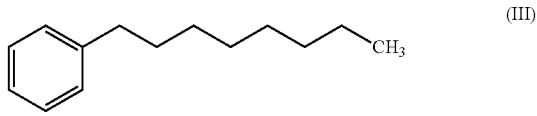
(III)

b) reacting the compound of formula (III) with a 3-halopropionyl halide to obtain a compound of formula (IV):

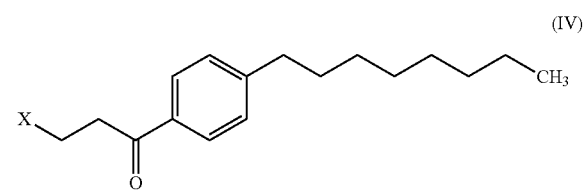
(IV)

wherein X is a halogen;

b) reacting the compound of formula (IV) with a compound of formula (V):

$M^{+n}(NO_2)_n$    (V)

wherein M is a metal ion and n is 1, 2, or 3 to obtain a compound of formula (VI); and

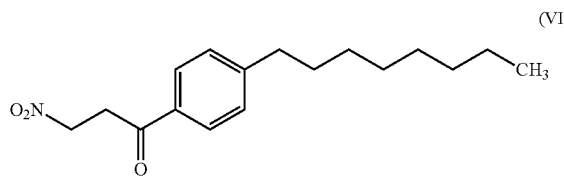

d) converting the compound of formula (VI) to fingolimod of formula (Ia):

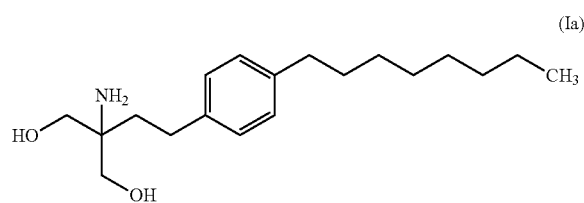 [SMILES: CCCCCCCCc1ccc(CCC(N)(CO)CO)cc1]

or its salt.

Step a) involves reducing octanophenone of formula (II) using a Lewis acid and a trialkyl silane to obtain octyl benzene of formula (III).

Lewis acids that may be used in the process of step a) may be selected from $TiCl_4$, $AlCl_3$, $BF_3$, or the like. The trialkylsilanes that may be used in the process of step a) may be selected from triethylsilane, trimethylsilane, triisopropyl silane, or the like. The amount of Lewis acid that may be used ranges from about 0.5 to about 3.0 molar equivalents per mole of the compound of formula (II) and the amount of trialkyl silane that may be used ranges from about 2.0 to about 3.0 molar equivalents or more per mole of the compound of formula (II).

In an embodiment, the reaction of step a) may be carried out using $TiCl_4$ and triethylsilane.

The process of step a) may be carried out in the presence a solvent selected from a halogenated hydrocarbon solvent such as dichloromethane, 1,2-dichloroethane, trichloroethylene, perchloroethylene, 1,1,1-trichloroethane, 1,1,2-trichloroethane, chloroform, carbon tetrachloride, or the like; a hydrocarbon solvent such as hexane, heptane, cyclohexane or the like; or mixtures thereof. The reaction of step a) may be carried out at temperatures ranging from about −40° C. to about 40° C. or more. In an embodiment, the reaction of step a) may be carried out at temperatures ranging from about −25° C. to about 25° C. In an embodiment, the reaction of step a) may be carried out at temperatures ranging from −10° C. to about 5° C.

After the completion of the reaction, the compound of formula (III) may optionally be isolated and purified or the reaction mass comprising the compound of formula (III) may be taken forward for the next step of the process. In an embodiment, the reaction mass comprising the compound of formula (III) is filtered through a hyflo bed and the filtrate is taken forward for the next step of the process.

Step b) involves reacting the compound of formula (III) with a 3-halopropionyl halide to obtain a compound of formula (IV).

The step of reacting the compound of formula (III) with 3-halopropionyl halide to obtain a compound of formula (IV) may be carried out in the presence of a Lewis acid and an organic solvent. Lewis acids that may be used in the process of step b) may be selected from $TiCl_4$, $AlCl_3$, $BF_3$, or the like. X in the compound of formula (IV) may be a chloro, bromo, or iodo. In an embodiment, the 3-halopropionyl halide that may be used in the process of step b) may be 3-chloropropionyl chloride. Organic solvents that may be used in the process of step b) may be selected from a halogenated hydrocarbon solvent such as but not limited to dichloromethane, 1,2-dichloroethane, trichloroethylene, perchloroethylene, 1,1,1-trichloroethane, 1,1,2-trichloroethane, chloroform, carbon tetrachloride, or the like. In an embodiment, the solvent selected in step b) is the same solvent used in step a).

The reaction of step b) may be carried out at temperatures ranging from about −40° C. to about 40° C. or more. In an embodiment, the addition of a Lewis acid and 2-halopropionyl halide to the reaction mass may be carried out at temperatures less than 10° C. and the reaction mass may be maintained at a temperature ranging from about −10° C. to about 10° C. until the completion of the reaction.

After the completion of the reaction, the compound of formula (IV) may optionally be isolated by techniques known in the art and purified or the reaction mass comprising the compound of formula (IV) may be taken forward for the next step of the process. In an embodiment, after the completion of the reaction, the reaction mass is added to water precooled to 5-10° C., organic layer is separated, washed with aqueous sodium bicarbonate solution and the resultant organic layer is optionally dried and concentrated under reduced pressure to obtain a compound of formula (IV). Optionally, the compound of formula (IV) may be further purified.

In an embodiment, the compound of formula (IV) may be purified using a hydrocarbon solvent such as hexane, heptane, cyclohexane or the like.

Step c) reacting the compound of formula (IV) with a compound of formula (V) to obtain a compound of formula (VI).

The compound of formula (V) $M^{+n}(NO_2)_n$ that may be used in step c) may be selected from lithium nitrite, sodium nitrite, potassium nitrite, silver nitrite, or the like. Step c) may be carried out in the presence of solvents that may be selected from but not limited to dimethylformamide, diethylformamide, dimethyl sulfoxide, tetrahydrofuran, acetone, acetonitrile, methanol, methanol/water, isopropyl alcohol, ethyl acetate, or mixtures thereof. The process of step c) may be carried at temperatures ranging from about −80° C. to about 80° C. or more based on the solvent employed. In an embodiment, step c) may be carried at temperatures ranging from about 25° C. to about 50° C. In another embodiment, step c) may be carried at temperatures ranging from about 30° C. to about 35° C.

In an embodiment, the compound of formula (IV) is reacted with sodium nitrite in the presence of ethyl acetate.

After the completion of the reaction, the compound of formula (VI) may optionally be isolated by techniques known in the art and optionally purified. In an embodiment, after the completion of the reaction, the reaction mass is added to water, added ethyl acetate, organic layer is separated, washed with aqueous sodium bicarbonate solution and/or brine solution and the resultant organic layer is dried and concentrated under reduced pressure to obtain a compound of formula (VI). Optionally, the compound of formula (VI) may be further purified from ethylacetate and n-hexane or by recrystallization using an alcohol selected from methanol, ethanol, isopropanol or the like.

Step d) involves converting the compound of formula (VI) to fingolimod of formula (Ia) or its salts.

The compound of formula (VI) may be converted to fingolimod or its salts by the processes known in the art for example CN1765872 or by the processes disclosed in the present application.

In an embodiment, the compound of formula (VI) is reacted with 10% Pd on carbon under a hydrogen atmosphere in the presence of methanol at 25-30° C. and in further steps is converted to fingolimod. After completion of reaction, fingolimod or its hydrochloride salt may be isolated according to known processes.

In an embodiment, the compound of formula (VI) is subjected to reduction using a Lewis acid and a trialkyl silane to obtain a compound of formula (VII), which in further steps is converted to fingolimod or its salts thereof.

In an aspect, the present application provides a process for the preparation of fingolimod of formula (Ia)

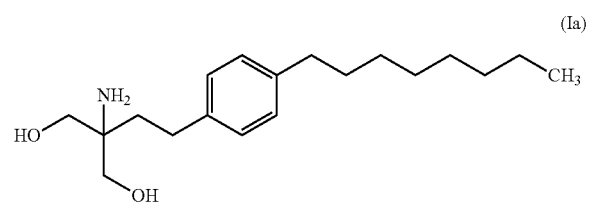 [SMILES: CCCCCCCCc1ccc(CCC(N)(CO)CO)cc1]
(Ia)

or its salt comprising:

a) reducing 3-nitro-1-(4-octylphenyl)propan-1-one of formula (VI):

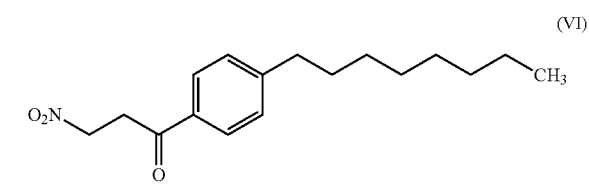 [SMILES: CCCCCCCCc1ccc(C(=O)CC[N+](=O)[O-])cc1]
(VI)

using a Lewis acid and a trialkyl silane to obtain a compound of formula (VII); and

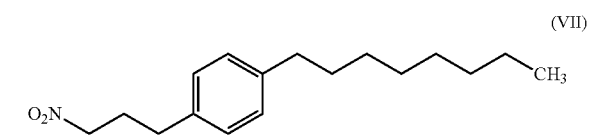 [SMILES: CCCCCCCCc1ccc(CCC[N+](=O)[O-])cc1]
(VII)

b) converting the compound of formula (VII) to fingolimod of formula (Ia):

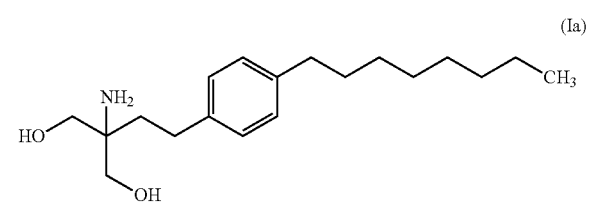 [SMILES: CCCCCCCCc1ccc(CCC(N)(CO)CO)cc1]
(Ia)

or its salt.

Step a) involves reducing the compound of formula (VI) using a Lewis acid and a trialkyl silane to obtain a compound of formula (VII). Lewis acids that may be used in the process of step a) may be selected from $TiCl_4$, $AlCl_3$, $BF_3$, or the like. Trialkyl silanes that may be used in the process of step a) may be selected from triethylsilane, trimethylsilane, triisopropyl silane, or the like. The amount of Lewis acid that may be used ranges from about 0.5 to about 3.0 molar equivalents per mole of the compound of formula (VI) and the amount of trialkyl silane that may be used ranges from about 2.0 to about 3.0 molar equivalents per mole of the compound of formula (VI).

The process of step a) may be carried out in the presence a solvent selected from a halogenated hydrocarbon solvent such as dichloromethane, 1,2-dichloroethane, trichloroethylene, perchloroethylene, 1,1,1-trichloroethane, 1,1,2-trichloroethane, chloroform, carbon tetrachloride, or the like; a hydrocarbon solvent such as hexane, heptane, cyclohexane or the like; or mixtures thereof. The reaction of step a) may be carried out at temperatures ranging from about −40° C. to about 40° C. or more. In an embodiment, the reaction of step a) may be carried out at temperatures ranging from about −25° C. to about 25° C. In an embodiment, the reaction of step a) may be carried out at temperatures ranging from about −10° C. to about 5° C. In an embodiment, the reaction of step a) may be carried out using $TiCl_4$ and triethylsilane.

After the completion of the reaction, the compound of formula (VII) may optionally be isolated and purified or the reaction mass comprising the compound of formula (VII) may be taken forward for the next step of the process. In an embodiment, the reaction mass comprising the compound of formula (VII) is filtered optionally through a hyflo bed to remove and the filtrate is taken forward for the next step of the process. In an embodiment, after the completion of the reaction, water precooled to 0-10° C. is added to reaction mass, organic layer is separated, washed with aqueous sodium bicarbonate solution and the resultant organic layer is optionally dried and concentrated under reduced pressure to obtain a compound of formula (VII).

Step b) involves converting the compound of formula (VII) to fingolimod or its salt. The compound of formula (VII) may be converted to fingolimod or its salts by the processes known in the art or by the processes disclosed in the present application.

In an embodiment, the compound of formula (VII) may be converted to fingolimod or its salt by processes comprising:

(i) reacting the compound of formula (VII):

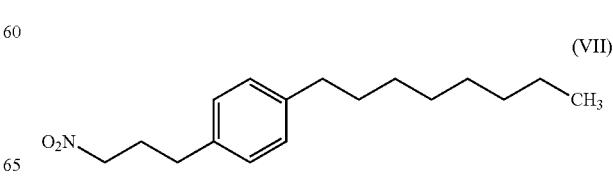
(VII)

with paraformaldehyde to obtain a compound of formula (VIII); and

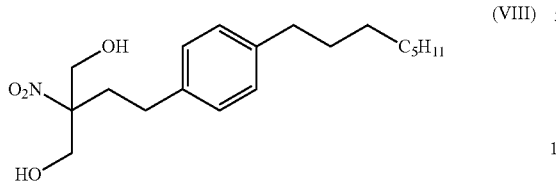

(ii) reacting the compound of formula (VIII) with a reducing agent to obtain fingolimod of formula (Ia):

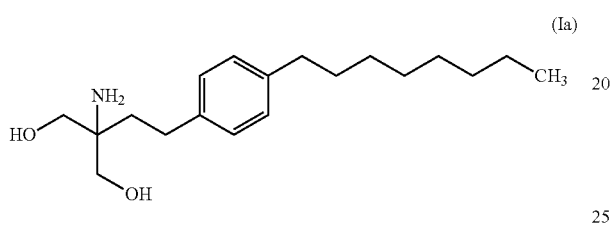

or its salt.

The compound of formula (VII) may be reacted with paraformaldehyde, in the presence of a base, to obtain the compound of formula (VIII). Suitable bases that may be used for this above step include, but are not limited to, organic bases such as diethylamine, triethylamine, n-butylamine, propylamine, diisopropylethylamine, dicyclohexylamine, or the like; inorganic bases such as sodium carbonate, potassium carbonate or the like. The process of step i) may be carried out in the presence of solvent, including alcohols such as methanol, ethanol, or the like; polar aprotic solvents such as dimethylformamide, dimethyl sulfoxide, tetrahydrofuran, acetone, acetonitrile, or the like; aromatic solvents such as toluene, xylene or the like or mixtures thereof. The reaction may be carried out at temperatures ranging from about 0° C. to about 65° C. or more based on the solvent employed.

Reducing agents that may be used in step ii) of this process include, but are not limited to: compounds such as sodium borohydride, lithium borohydride, or lithium aluminium hydride; or Pd on carbon, Raney® nickel, or Pd(OH)$_2$, under a hydrogen atmosphere. The reduction process of step ii) may be carried out in the presence a solvent, including: alcohols such as methanol, ethanol, tert-butyl alcohol, or the like; tetrahydrofuran; diethyl ether; dioxane; acetone; ethyl acetate; toluene; etc. The reduction may be carried out at temperatures ranging from about 0° C. to about 45° C. or higher or about 25° C. to about 35° C., based on the reagents and solvents employed. In particular embodiment, the compound of formula (VIII) is reacted with 10% Pd on carbon under a hydrogen atmosphere in the presence of methanol at 25-30° C., to give fingolimod. After completion of reaction, fingolimod or its salts may be isolated according to known processes, or by processes disclosed in the present application.

In an embodiment, the present application provides process for the preparation of fingolimod of formula (Ia) or its salt comprising:

a) reducing 3-nitro-1-(4-octylphenyl)propan-1-one of formula (VI):

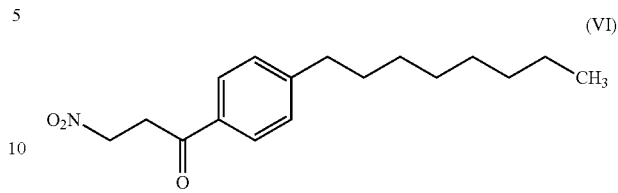

using a Lewis acid and a trialkyl silane to obtain a compound of formula (VII); and

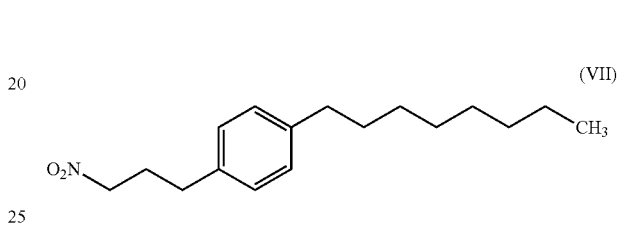

b) reacting the compound of formula (VII):

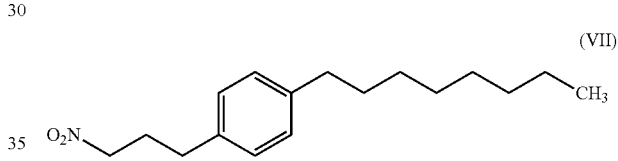

with paraformaldehyde to obtain a compound of formula (VIII); and

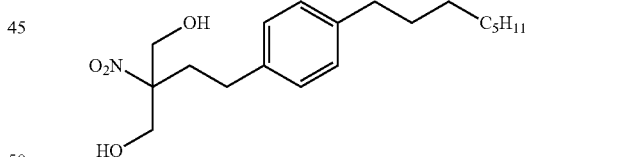

c) reacting the compound of formula (VIII) with a reducing agent to obtain fingolimod of formula (Ia):

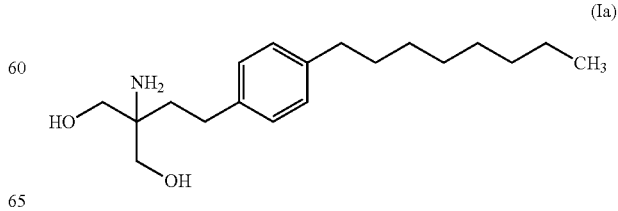

or its salt.

The above steps may be carried out according to the process described in the present application.

In an embodiment, the present application provides process for the preparation of fingolimod of formula (Ia):

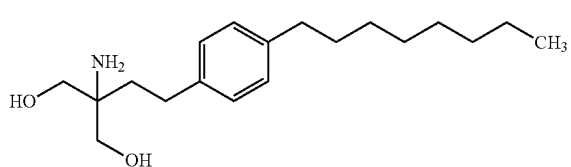
(Ia)

or its salt comprising:

(a) reacting the compound of formula (VII):

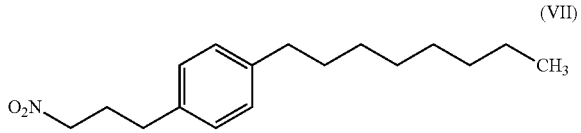 [SMILES: CCCCCCCCc1ccc(CCC[N+](=O)[O-])cc1]
(VII)

with paraformaldehyde in the presence of potassium carbonate to obtain a compound of formula (VIII); and

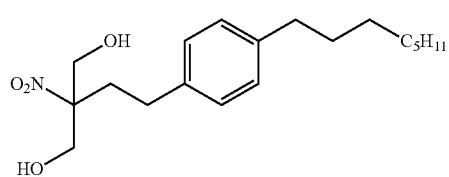
(VIII)

(b) reacting the compound of formula (VIII) with a reducing agent to obtain fingolimod of formula (Ia) or its salt.

In an aspect, the present application provides a process comprising reducing octanophenone of formula (II):

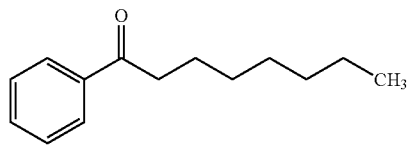
(II)

using a Lewis acid and a trialkyl silane to obtain octylbenzene of formula (III):

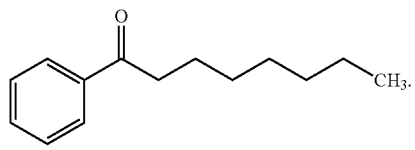
(III)

In an aspect, the present application provides the process further comprising reacting the compound of formula (III) with a 3-halopropionyl halide to obtain a compound of formula (IV):

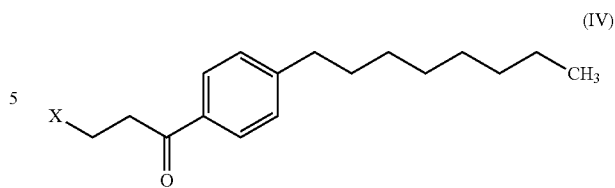
(IV)

wherein X is a halogen.

In an aspect, the present application provides the process further comprising reacting the compound of formula (IV) with a compound of formula (V):

$M^{+n}(NO_2)_n$ (V)

wherein M is a metal ion and n is 1, 2, or 3 to obtain a compound of formula (VI):

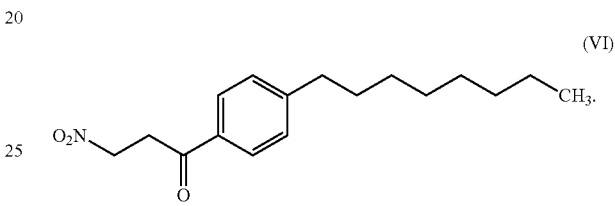
(VI)

In an aspect, the present application provides a process comprising reducing 3-nitro-1-(4-octylphenyl)propan-1-one of formula (VI):

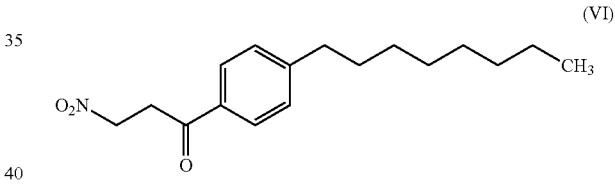
(VI)

using a Lewis acid and a trialkyl silane to obtain a compound of formula (VII):

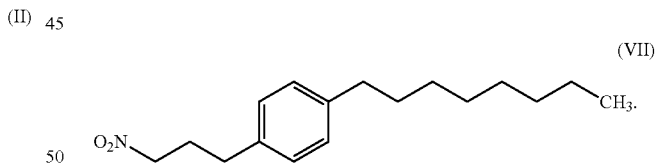
(VII)

In an aspect, the present application provides processes for the preparation of fingolimod or its salt, embodiments comprising:

a) reacting the compound of formula (IX),

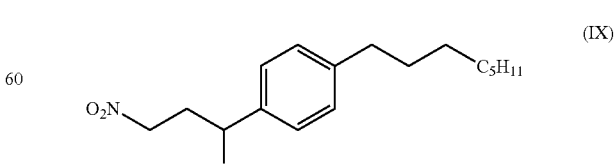
(IX)

with a reducing agent, to obtain the compound of formula (VII); and

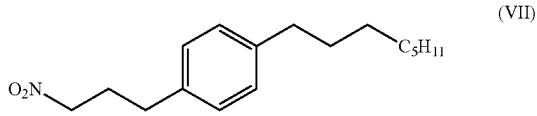

b) converting the compound of formula (VII) to fingolimod or its salt.

Step a) involves reacting the compound of formula (IX) with a reducing agent to obtain the compound of formula (VII).

The compound of formula (IX) may be obtained by any process, including processes described in the literature. For example, the compound of formula (IX) may be prepared by the process described in Chinese Patent Publication 1765872, or by a process described in the present application.

Reducing agents that may be used in step a) include, without limitation thereto, Pd on carbon, Raney nickel, and Pd(OH)$_2$, under a hydrogen atmosphere, or triethylsilane and trifluoroacetic acid.

In embodiments, triethylsilane and trifluoroacetic acid is used as the reducing agent.

Step b) involves converting the compound of formula (VII) to fingolimod or its salt.

The compound of formula (VII) may be converted to fingolimod or its salts by a process described in the present application.

In embodiments, the compound of formula (VII) may be converted to fingolimod or its salt by processes comprising:

(i) reacting the compound of formula (VII),

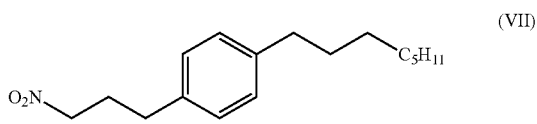

with paraformaldehyde to obtain a compound of formula (VIII); and

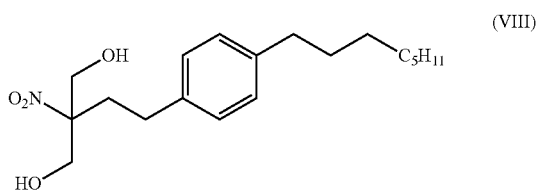

(ii) reacting the compound of formula (VIII) with a reducing agent to obtain fingolimod or its salt.

The compound of formula (VII) can be reacted with paraformaldehyde, in the presence of a base, to obtain the compound of formula (VIII).

Suitable bases that may be used for this above step include, but are not limited to, organic bases such as diethylamine, triethylamine, n-butylamine, propylamine, disiopropylethylamine, dicyclohexylamine, and the like.

The process of step i) may be carried out in the presence a solvent, including alcohols such as methanol, ethanol, and the like, and the reaction may be carried out at temperatures ranging from about 0° C. to about 40° C., or about 25° C. to about 35° C.

Reducing agents that may be used in step ii) of this process include, but are not limited to: compounds such as sodium borohydride, lithium borohydride, and lithium aluminium hydride; Pd on carbon, Raney nickel, and Pd(OH)$_2$, under a hydrogen atmosphere.

The reduction process of step ii) may be carried out in the presence a solvent, including: alcohols such as methanol, ethanol, tert-butyl alcohol, and the like; tetrahydrofuran; diethyl ether; dioxane; acetone; ethyl acetate; toluene; etc. The reduction may be carried out at temperatures ranging from about 0° C. to about 45° C. or higher, or about 25 to about 35° C., based on the reagents and solvents employed.

In particular embodiments, the compound of formula (VIII) are reacted with 10% Pd on carbon under a hydrogen atmosphere in the presence of ethanol at 25-35° C., to give fingolimod. After completion of reaction, fingolimod or its salts may be isolated according to known processes, or by processes disclosed in the present application.

It has been found that repeating the process sequence involving the reactions of the compound of formula (IX) with paraformaldehyde and triethylamine, followed by reduction of the hydroxyl function group adjacent to the phenyl group, using the conditions disclosed in Chinese Patent Publication 1765872, does not result in the desired product. Further, it has been found that the step of reducing the hydroxyl functional group adjacent to the phenyl group gives multiple spots by a thin layer chromatography analysis, and may be the reason for the low reported yield.

It was surprisingly found that altering the reaction sequence as described herein provides higher yield and purity of the fingolimod.

In an aspect, the present application provides processes for the preparation of fingolimod or salt thereof, embodiments comprising:

a) reacting the compound of formula (VII),

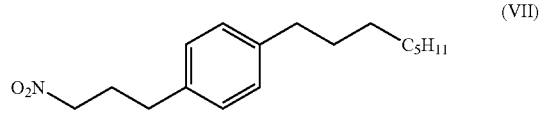

with paraformaldehyde in the presence of a base, to obtain the compound of formula (VIII); and

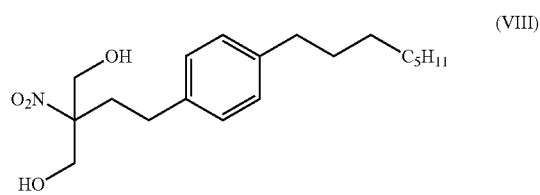

b) converting the compound of formula (VIII) to fingolimod or its salt.

Step a) involves reacting a compound of formula (VII) with paraformaldehyde in the presence of a base, to obtain the compound of formula (VIII).

Suitable bases that may be used for this step include, but are not limited to, organic bases such as diethylamine, triethylamine, n-butylamine, propylamine, disiopropylethylamine, dicyclohexylamine, and the like.

The process of step a) may be carried out in the presence a solvent, including alcohols such as methanol, ethanol, and the like, and the reaction may be carried out at temperatures ranging from about 0° C. to about 40° C., or about 25 to about 35° C.

It has been found that the above step as per the processes described in the literature using Amberlyst A-21 resulted in product with high content of the starting material.

It has been found that the rate of reaction completion is accelerated in the presence of a base, and the product is obtained with high yields and purity.

Step b) converting the compound of formula (VIII) to fingolimod or its salt.

The step of converting the compound of formula (VIII) to fingolimod or its salts may be carried out by using reducing agents.

Reducing agents that may be used in step b) include, but are not limited to: compounds such as sodium borohydride, lithium borohydride, and lithium aluminium hydride; metals such as palladium on carbon, platinum oxide, and Raney nickel, $Pd(OH)_2$ under a hydrogen atmosphere.

The reduction process of step b) may be carried out in the presence a solvent, including, but not limited to: alcohols such as methanol, ethanol, tert-butyl alcohol, and the like; tetrahydrofuran; diethyl ether; dioxane; acetone; ethyl acetate; toluene; etc. The reduction may be carried out at temperatures ranging from about 0° C. to about 45° C. or higher, or about 25 to about 35° C., based on the reagents and solvents employed.

In particular embodiments, the compound of formula (VIII) are reacted with 10% Pd on carbon under a hydrogen atmosphere in the presence of ethanol at 25-35° C., to give fingolimod. After completion of reaction, fingolimod or its salts may be obtained according to known processes, or by processes disclosed in the present application.

In an embodiment, fingolimod hydrochloride may be obtained by dissolving fingolimod of step b) in ethanol, cooling the reaction mixture to 0° C. to 5° C., adding ethanolic hydrochloride solution drop wise over a period of 10 to 30 minutes at the same temperature to obtain a suspension, maintaining the suspension at the same temperature for 1 to 3 hours, filtering the obtain solid, washing with an ether solvent and optionally drying the product obtained to give fingolimod hydrochloride.

In an aspect, the present application provides processes for the preparation of fingolimod or its salt thereof, embodiments comprising:

a) reacting the compound of formula (IX),

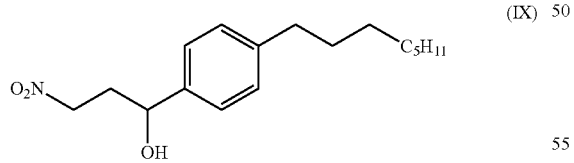

(IX)

with a reducing agent to obtain the compound of formula (VII);

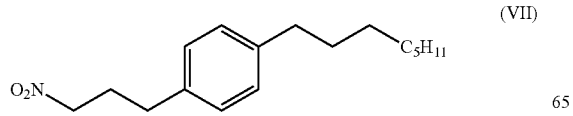

(VII)

b) reacting the compound of formula (VII) with paraformaldehyde to obtain the compound of formula (VIII); and

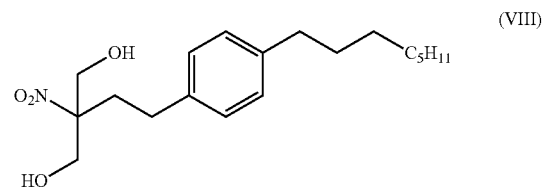

(VIII)

c) converting the compound of formula (VIII) to fingolimod or its salt.

In an aspect, the present application provides processes for the preparation of fingolimod or its salt, embodiments comprising:

a) reacting a compound of formula (X),

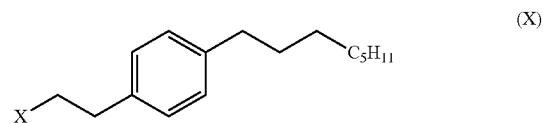

(X)

wherein X is a leaving group, with a compound of formula (XI),

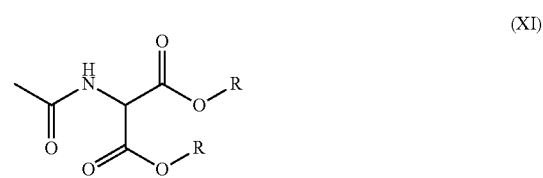

(XI)

wherein R is a $C_1$-$C_4$ alkyl group, in the presence of a metal carbonate, to give a compound of formula (XII);

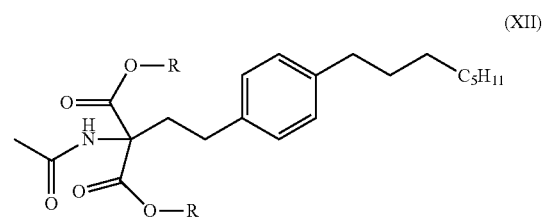

(XII)

b) reacting the compound of formula (XII) with a reducing agent to provide the compound of formula (XIII); and

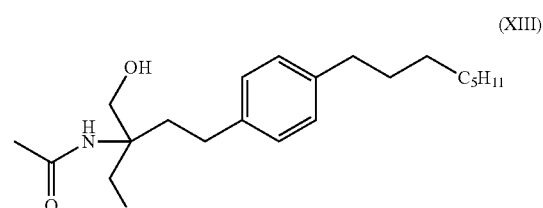

(XIII)

c) converting the compound of formula (XIII) to fingolimod or its salt.

Step a) involves reacting a compound of formula (X) with a compound of formula (XI) in the presence of a metal carbonate, to give a compound of formula (XII).

The compound of formula (X) may be obtained using any process, including processes described in the literature. For example, the compound of formula (X) may be prepared by a process described in U.S. Pat. No. 5,604,229 or by a process described in the present application.

Leaving groups that may be used in the process of step a) may be halogen groups, such as chloro, bromo, iodo, and the like.

$C_1$-$C_4$ alkyl groups for the compound of formula (XI) may be, for example, methyl, ethyl, isopropyl, and the like.

Metal carbonates that may be used in the step include sodium carbonate, potassium carbonate, cesium carbonate, and the like.

Typical amounts of metal carbonate used in step a) range from about 1 to about 4 molar equivalents, per molar equivalent of the compound of formula (X).

It has been found that the use of sodium methoxide or sodium ethoxide in the above step, as in processes described in the literature, result in low yields and a product having high concentrations of impurities, for example the undesired compound of formula (A).

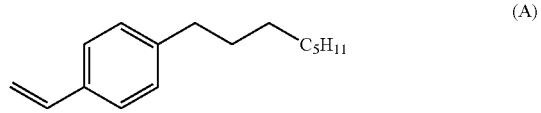

(A)

This finding is supported by N. Matsumoto et al., "Synthesis of the Key Intermediate, Diethyl 2-Acetylamino-2-(2-(4-octanoylphenyl)ethyl)propane-1,3-dioate, of the Immunomodulatory Agent FTY720 (Fingolamod)," *Chemical & Pharmaceutical Bulletin*, Vol. 56(4), pages 595-597, 2008 wherein the compound of formula (A) is prepared by reacting the compound of formula (X) (where X is Br) with sodium ethoxide, in the presence of ethanol and at a temperature of 60° C., for 1 hour.

It has been found that the rate of reaction completion is accelerated in the presence of metal carbonates, and the product is obtained with high yields and purity, e.g., with a content of the impurity compound of formula (A) less than about 10%, or less than about 5%, or less than about 1%, or less than about 0.5%.

The reaction of step a) may be carried out in the presence of a solvent. Useful solvents include, without limitation thereto, polar aprotic solvents such as dimethylsulphoxide, N,N-dimethylformamide, N-methylpyrrolidone, tetrahydrofuran, acetonitrile, and the like.

The reaction may be carried out at temperatures ranging from about 25° C. to about 100° C., or about 60° C. to about 90° C.

After the completion of the reaction, the compound of formula (XII) may be isolated and optionally purified.

In a particular embodiment, the compound of formula (X) is reacted with the compound of formula (XI) in the presence of cesium carbonate and dimethylsulfoxide, to give a compound of formula (XII).

Step b) involves reacting the compound of formula (XII) with a reducing agent, to provide a compound of formula (XIII).

Reducing agents that may be used include, but are not limited to, sodium borohydride, lithium aluminium hydride, and the like.

The amounts of reducing agents that may be used range from about 1 to about 8 molar equivalents, per molar equivalent of the compound of formula (XII).

The process of step b) may be carried out in the presence a solvent, for example the alcohols methanol, ethanol, and the like, and the reaction may be carried out at temperatures ranging from about 0° C. to about 40° C., or about 25° C. to about 35° C.

In a particular embodiment, the compound of formula (XII) is reacted with sodium borohydride, in the presence of methanol, to give a compound of formula (XIII).

After completion of the reaction, the compound of formula (XIII) may be isolated and optionally purified. In embodiments, after completion of the reaction, the reaction mixture is optionally concentrated to form a solid, dissolved in water, and extracted with an organic solvent, such as ethyl acetate. The organic extract is washed with water and then brine solution, and concentrated under reduced pressure to give the compound of formula (XIII). The product obtained can be further purified by column chromatography, such as using 100-200 mesh silica gel and ethyl acetate-hexane as the eluent system.

Step c) converting the compound of formula (XIII) to fingolimod or its salts

The step of converting the compound of formula (XIII) to fingolimod or its salts may be carried out by hydrolysis using an acid or a base.

The acids that may be used include mineral acids such as aqueous hydrochloric acid, aqueous sulphuric acid, aqueous phosphoric acid, aqueous perchloric acid, aqueous hydrobromic acid, or carriers containing an acid such as acidic resins. The bases that may be used include, but are not limited to, aqueous methylamine, aqueous ammonia, and iodine in methanol.

In a particular embodiment, an acid that may be used in the above step includes aqueous hydrochloric acid having concentrations about 0.5N to about 5N.

The reaction may be carried out at temperatures ranging from about 0° C. to about reflux temperatures. After completion of reaction, fingolimod or its salts may be isolated according to known processes, or by processes disclosed in the present application.

In an aspect, the present application provides processes for the preparation of fingolimod hydrochloride, embodiments comprising;

a) reacting the compound of formula (Xa),

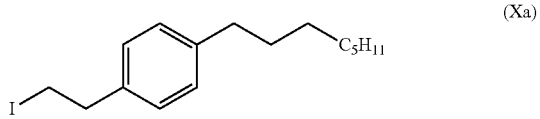

(Xa)

with the compound of formula (XIa),

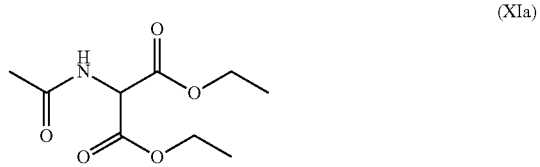

(XIa)

in the presence of a metal carbonate, to give the compound of formula (XIIa);

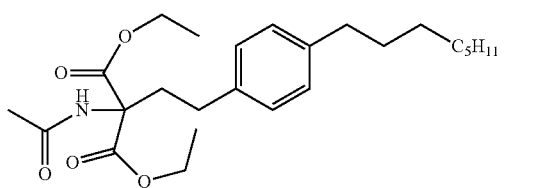

(XIIa)

b) reacting the compound of formula (XIIa) with a reducing agent to provide the compound of formula (XIII); and

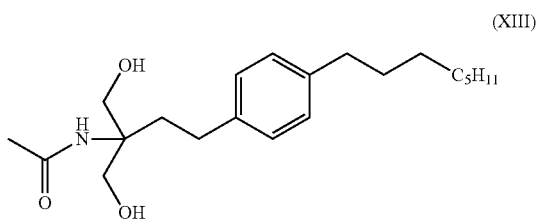

(XIII)

c) converting the compound of formula (XIII) to fingolimod or its hydrochloride its salts.

In an aspect the present application provides process for the purification of fingolimod hydrochloride comprising:

(a) providing a solution of fingolimod hydrochloride in methanol or methanol and ethylacetate mixture;

(b) optionally adding ethylacetate;

(c) cooling the solution to a temperature below 10° C.;

(d) isolating fingolimod hydrochloride.

Providing a solution in step a) includes obtaining a solution of fingolimod hydrochloride in methanol or methanol and ethylacetate mixture as a final step in the preparation of the compound or dissolving fingolimod hydrochloride in methanol or dissolving fingolimod hydrochloride in methanol and adding ethyl acetate or vice-versa or dissolving fingolimod hydrochloride in methanol and ethylacetate mixture.

The solution in step a) may be provided at any temperature ranging from about 0° C. to about bailing point of the solvent, and preferably at temperatures about 20° C. to about 35° C., more preferably at temperatures about 25° C. to about 30° C.

The solution may optionally be treated with activated charcoal and then filtered to remove the carbon.

The solution may optionally be filtered by passing through paper, glass fiber, or other membrane material, or a bed of a clarifying agent such as Celite. Depending upon the equipment used, as well as the concentration and temperature of the solution, the filtration apparatus may need to be heated or cooled to avoid undesired crystallization.

Optionally, ethylacetate may be added to the solution obtained in step a). In an embodiment, ethylacetate is added to the solution obtained in step a) and taken forward for the next step.

The solution obtained in step a) or step b) may be cooled to a temperature below 10° C. to precipitate the solid. In embodiments, the solution may be cooled to temperatures about 0° C. to about 5° C.

The solid obtained from step c) may be collected using known techniques.

Drying may be suitably carried out using any of equipment at atmospheric pressure or under reduced pressures, at temperatures less than about 40° C., less than about 30° C., less than about 20° C. and any other suitable temperatures. The drying may be carried out for any time periods required for obtaining a desired quality, such as from about 15 minutes to several hours, or longer.

In an aspect, the present application provides amorphous fingolimod hydrochloride.

In an aspect, the present application provides processes for the preparation of amorphous fingolimod hydrochloride, embodiments comprising:

a) providing a solution of fingolimod hydrochloride and a pharmaceutically acceptable carrier in a solvent; and b) obtaining amorphous fingolimod hydrochloride.

Step a) involves providing a solution of fingolimod hydrochloride and a pharmaceutically acceptable carrier in a solvent.

Providing a solution in step a) includes obtaining a solution of fingolimod hydrochloride in a solvent, as a final step in the preparation of the compound, and dissolving a pharmaceutically acceptable carrier in the solution, or dissolving fingolimod hydrochloride in a suitable solvent, along with a pharmaceutically acceptable carrier. Alternatively, a solution containing the fingolimid hydrochloride and a separate solution containing a pharmaceutically acceptable carrier can be combined.

Any polymorphic form of fingolimod hydrochloride may be utilized for providing the solution of fingolimod hydrochloride in step a).

Fingolimod hydrochloride that may be used as the input for a process of the present application may be obtained by any process, including the processes described in the literature. For example, fingolimod hydrochloride may be prepared by the processes described in U.S. Pat. No. 5,604,229.

Suitable solvents that may be used in step a) include, but are not limited to, water, alcohols such as methanol, ethanol, n-propanol, n-butanol, and any mixtures of two or more thereof.

Pharmaceutically acceptable carriers that may be used in this step include a polyvinylpyrrolidone (povidone or PVP), a hydroxypropyl cellulose (HPC), a hydroxypropyl methylcellulose (hypromellose or HPMC), a hydroxyethyl cellulose (HEC), and the like. Any mixtures of two or more thereof also will be useful. In specific embodiments, a pharmaceutically acceptable carrier is a povidone K-30 grade.

The dissolution temperatures may range from about −20° C. to about the reflux temperature of the solvent, depending on the solvent used for dissolution, as long as a clear solution of fingolimod hydrochloride is obtained without affecting its quality. Optionally, the solution may be filtered to remove any insoluble particles. The insoluble particles may be removed suitably by filtration, centrifugation, decantation, and any other suitable techniques. The solution may be filtered by passing through cloth, paper, glass fiber, or other membrane material. Depending upon the equipment used and the concentration and temperature of the solution, the filtration apparatus may need to be preheated to maintain the solution Step b) involves obtaining an amorphous fingolimod hydrochloride from the solution of step a).

In embodiments, the product may be obtained by removing solvent. Suitable techniques that may be used for the removal of solvent include, but are not limited to, using a rotational distillation device such as a Büchi® Rotavapor®, spray drying, thin-film drying, freeze-drying (lyophilization), etc.

The solvent may be removed, optionally under reduced pressures, at temperatures less than about 150° C., less than about 100° C., less than about 40° C., less than about 20° C., less than about 0° C., less than about −20° C., less than about −40° C., less than about −60° C., less than about −80° C., and any other suitable temperatures.

Freeze drying (lyophilization) may be carried out by freezing a solution of fingolimod hydrochloride at low temperatures and reducing the pressure as required removing the solvent from the frozen solution of fingolimod hydrochloride. Temperatures that may be required to freeze the solution, depend on the solvent chosen to make the solution of fingolimod hydrochloride, may range from about −60° C. to about 0° C., or up to about 45° C. Temperatures that may be required to remove the solvent from the frozen solution may be less than about 45° C., less than about 0° C., less than about −20° C., less than about −40° C., less than about −60° C., and any other suitable temperatures.

Spray drying may be carried out by evaporating a solution of fingolimod hydrochloride at temperatures up to the boiling point of the solvent.

The solid obtained from step b) may be collected using techniques such as scraping, shaking the container, or other techniques specific to the equipment used. The product thus obtained may optionally be further dried to improve its purity.

Drying may be suitably carried out using any of equipment such as a gravity oven, spray dryer, tray dryer, vacuum oven, Büchi® Rotavapor®, air oven, fluidized bed dryer, spin flash dryer, flash dryer, and the like. The drying may be carried out at atmospheric pressure or under reduced pressures, at temperatures less than about 80° C., less than about 60° C., less than about 40° C., less than about 20° C., less than about 0° C., and any other suitable temperatures. The drying may be carried out for any time periods required for obtaining a desired quality, such as from about 15 minutes to several hours, or longer.

The dried product may optionally be milled to obtain desired particle sizes. Milling or micronization may be performed before drying, or after the completion of drying of the product. Techniques that may be used for particle size reduction include, without limitation, ball, roller, and hammer mills, and jet mills.

Figure 2:
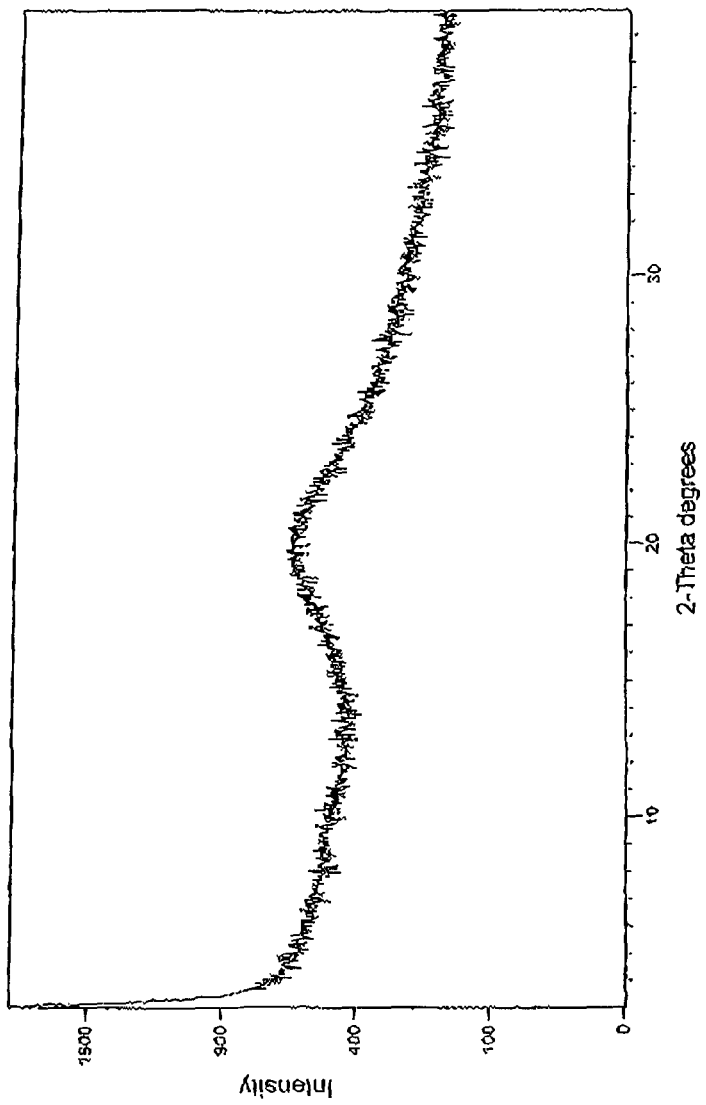
FIG. 2 is an illustration of a powder X-ray diffraction (PXRD) pattern of amorphous fingolimod hydrochloride, prepared according to Example 11.
Figure 3:
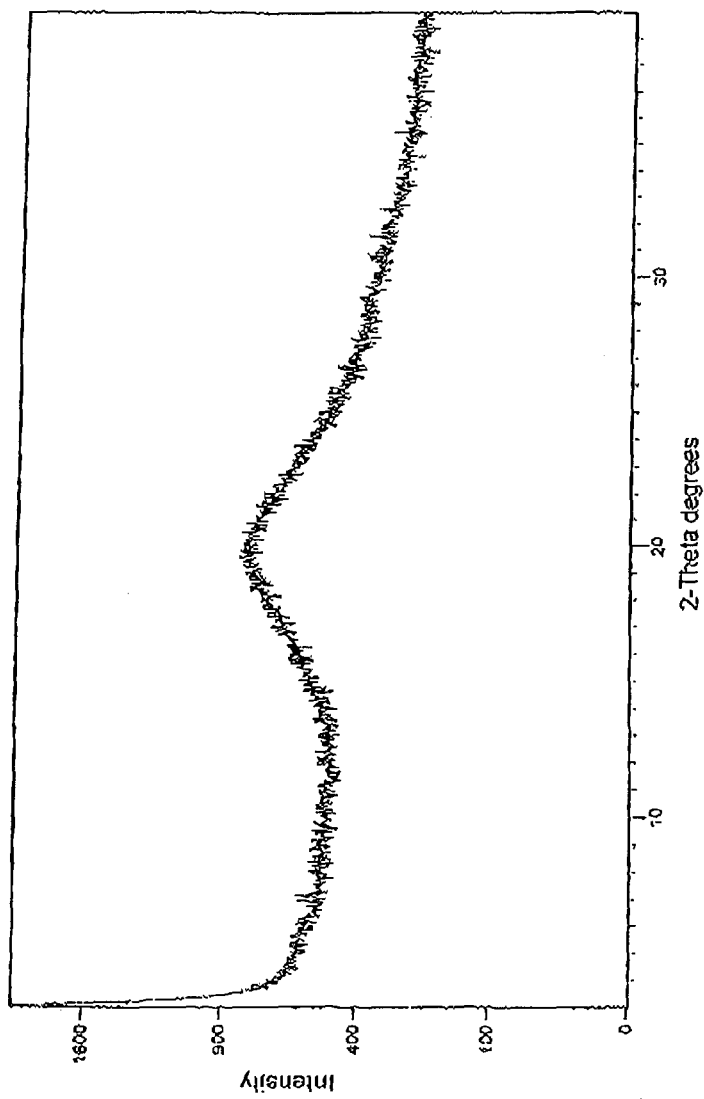
FIG. 3 is an illustration of a PXRD pattern of amorphous fingolimod hydrochloride, prepared according to Example 12.
Figure 4:
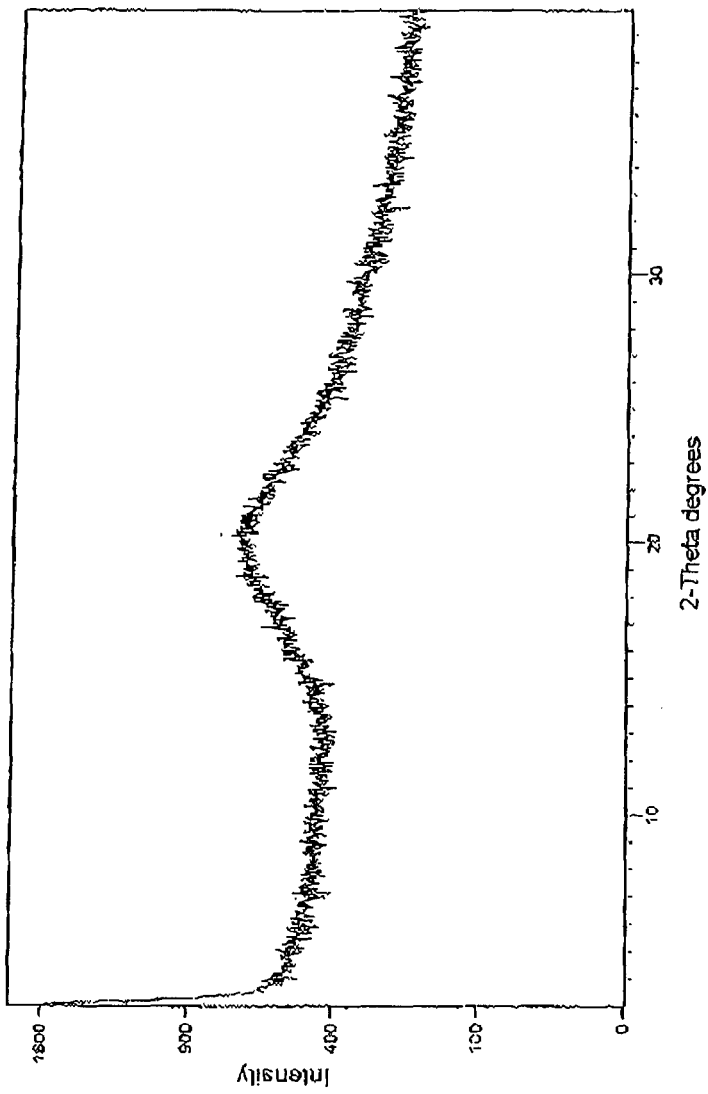
FIG. 4 is an illustration of a PXRD pattern of amorphous fingolimod hydrochloride, prepared according to Example 13.

In an aspect, the present application provides an amorphous fingolimod hydrochloride, characterized by a PXRD pattern substantially as illustrated by any one or more of FIG. 2, FIG. 3, and FIG. 4.

All PXRD data reported herein are obtained using a Bruker AXS D8 Advance Powder X-ray Diffractometer, or a PANalytical X-ray Diffractometer, with copper Kα radiation.

In an aspect, the present application provides pharmaceutical compositions comprising amorphous fingolimod hydrochloride, together with one or more pharmaceutically acceptable excipient.

Pharmaceutically acceptable excipients include, but are not limited to, suitable surface modifiers. Such excipients include various polymers, low molecular weight oligomers, natural products, and surfactants.

In an embodiment, the processes of the present application provides fingolimod hydrochloride having a purity greater than about 99.9% as determined using HPLC.

In another aspect, the present application provides fingolimod hydrochloride having purity greater than about 99.9% and less than about 0.1% of Impurity D and less than 0.1% of Impurity E as determined using HPLC.

In another aspect, the present application provides fingolimod hydrochloride having purity greater than about 99.9% and less than about 0.1% of Impurity F and less than 0.1% of Impurity Gas determined using HPLC.

In yet another aspect, the present application provides fingolimod hydrochloride having purity greater than about 99.8% and with less than about 0.1% of each of the compound given in the table below:

| Code | Structure |
| --- | --- |
| Impurity A | 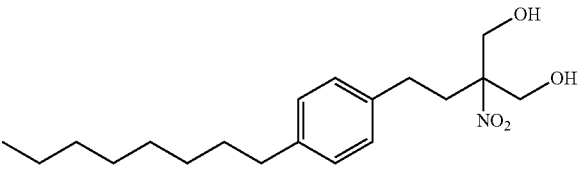 [SMILES: CCCCCCCCc1ccc(CCC(CO)(CO)[N+](=O)[O-])cc1] |
| Impurity B | 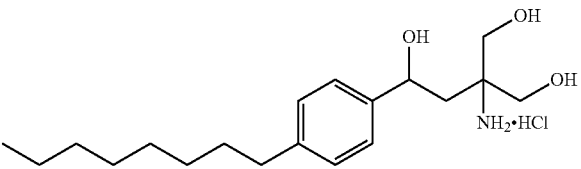 |
| Impurity C | 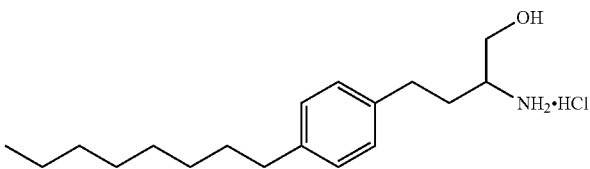 |
| Impurity D | 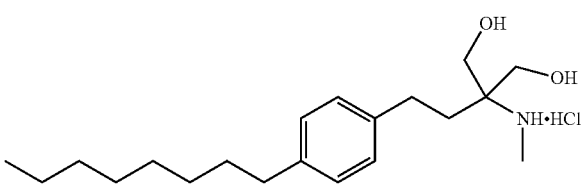 |

| Code | Structure |
|---|---|
| Impurity E | 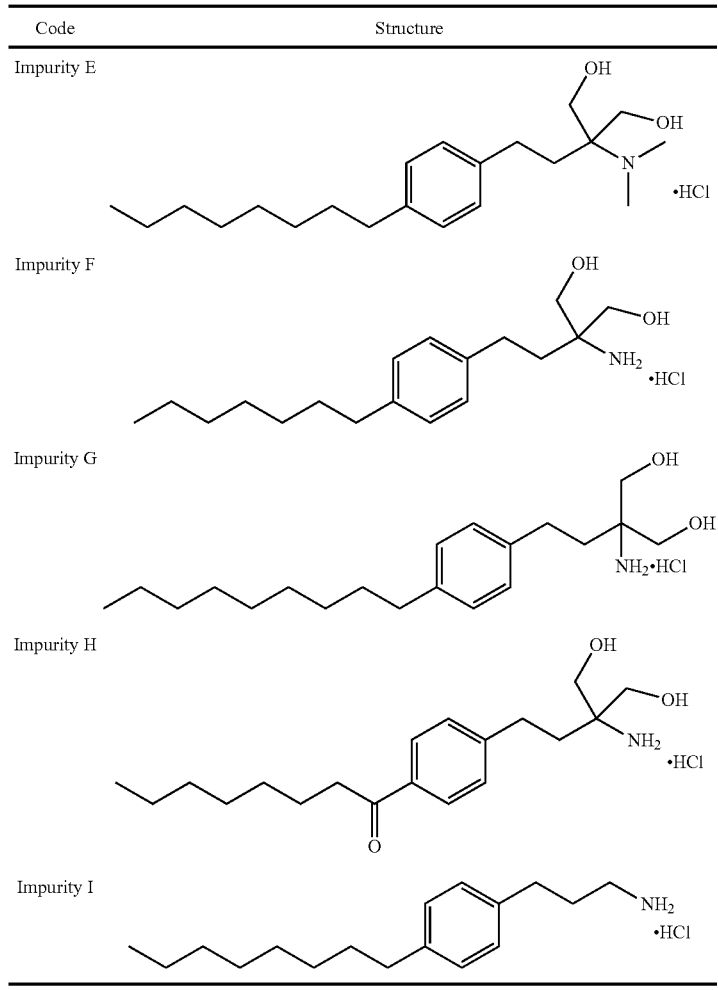 |
| Impurity F | 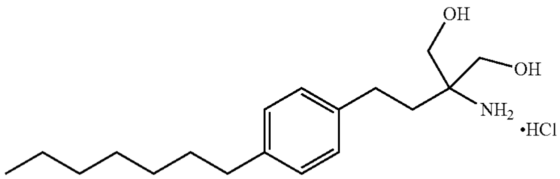 [SMILES: CCCCCCCc1ccc(CCC(N)(CO)CO)cc1 ; Cl] |
| Impurity G | 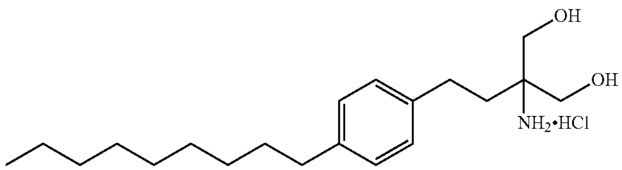 |
| Impurity H | 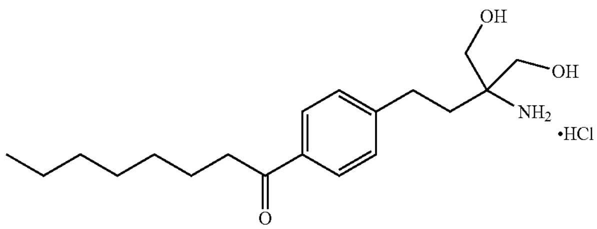 [SMILES: CCCCCCCC(=O)c1ccc(CCC(N)(CO)CO)cc1 ; Cl] |
| Impurity I | 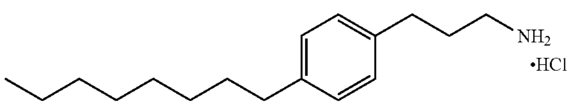 [SMILES: CCCCCCCCc1ccc(CCCN)cc1 ; Cl] |

The purity of fingolimod hydrochloride and its related substances or impurities may be analyzed using various methods. A representative useful HPLC method is described below.

Column: X Bridge C18, 150×4.6 mm, 3.5 μm
Column temperature: 60±2° C.
Injection volume: 10 μl
Diluent: Water:Acetonitrile (70:30)
Run time: 70 min
Mobile Phase A: Add 1.0 g of Tetrabutyl ammonium hydrogen sulphate (TBAHS) and 0.2 ml of ortho phosphoric acid to 1000 ml water, dissolve by sonication, filter and degass
Mobile Phase B: Mix Acetonitrile and water in the ratio of 9:1, filter and degass.
Flow rate: 1.0 ml/min
Wavelength of detection: 218 nm
Program: Gradient
Gradient program:

| Time (min) | % A | % B |
|---|---|---|
| 0 | 70 | 30 |
| 30 | 50 | 50 |
| 35 | 20 | 80 |
| 40 | 20 | 80 |
| 45 | 0 | 100 |
| 50 | 0 | 100 |
| 50.1 | 70 | 30 |
| 70 | 70 | 30 |

In an aspect, the present application provides a crystalline fingolimod freebase, characterized by a PXRD pattern substantially as illustrated by FIG. 1.

The crystalline fingolimod freebase may be prepared by a procedure as depicted in Example 10 of the present application.

The X-ray powder diffraction patterns described herein were generated using a Bruker AXS D8 Advance powder X-ray diffractometer, with a copper $K_\alpha$ radiation source (1.5418 Å). Generally, a diffraction angle (2θ) in powder X-ray diffractometry may have a permissible variation in the range of ±0.2°. Therefore, the aforementioned diffraction angle values should be understood as including values in the range of about ±0.2°. Accordingly, the present disclosure includes not only crystals whose peak diffraction angles in powder X-ray diffractometry completely coincide with each other, but also crystals whose peak diffraction angles coincide with each other with a permissible variation of about ±0.2°. Although the intensities of peaks in the x-ray powder diffraction patterns of different batches of a compound may vary slightly, the peaks and the peak locations are characteristic for a specific polymorphic form. The relative intensities of the PXRD peaks can vary depending on the sample preparation technique, crystal size distribution, various filters used, the sample mounting procedure, and the particular instrument employed. Moreover, instrument variation and other factors can affect the 2-theta values.

Certain specific aspects and embodiments of the present application will be explained in detail with reference to the following examples, which are provided only for purposes of illustration and should not be construed as limiting the scope of the application in any manner.

EXAMPLES

Example 1

Preparation of 3-chloro-1-(4-octylphenyl)propan-1-one

Octanophenone (50 g), dichloromethane (250 mL), and triethylsilane (69.77 g) are charged into a round bottom flask, stirred, and cooled to 0-10° C. Titanium tetrachloride (55.7 g) in dichloromethane (250 mL) is added to the reaction mixture over 30-35 minutes at temperature below 10° C. and the reaction mixture is stirred at a temperature of 25-30° C. for about 1 hour. The reaction mixture is filtered through a hyflo bed and washed with dichloromethane (100 mL). The filtrate obtained is charged into a second round bottom flask, aluminium chloride (41.6 g) is added, and the reaction mixture is cooled to 0-5° C. 3-Chloropropionyl chloride (30.47 g) in dichloromethane (50 mL) is added slowly to the reaction mixture at temperature below 5° C. and the reaction mixture is allowed to a temperature of 25-30° C. and maintained at the same temperature for about 1 hour. The reaction mixture is slowly added to water (500 mL) precooled to 0° C. and stirred. The organic layer is separated, washed with aqueous sodium bicarbonate solution (2×500 mL), water (500 mL), followed by brine solution (100 mL), dried over sodium sulphate and concentrated under reduced pressure at a temperature of about 45° C. to obtain 3-chloro-1-(4-octylphenyl)propan-1-one.

Example 2

Preparation of 3-nitro-1-(4-octylphenyl)propan-1-one (Formula VI)

3-Chloro-1-(4-octylphenyl)propan-1-one obtained in Example 1 and dimethylformamide (250 mL) are charged into a round bottom flask and stirred for dissolution at 25-30° C. Sodium nitrite (25.66 g) is charged into the flask and the reaction mixture is stirred 25-30° C. for about 90 minutes. The reaction mixture is added to a mixture of water (500 mL) precooled to 0-5° C. and ethyl acetate (250 mL), stirred, and the organic layer is separated. The aqueous layer is extracted with ethyl acetate (250 mL) and the organic layer is combined with the initial organic layer. The combined organic layer is washed with water (250 mL) followed by brine solution (100 mL), dried over sodium sulphate (50 g), and evaporated under reduced pressure at 45° C. to obtain the crude compound. The crude compound is dissolved in hexane (500 mL) at 26° C., is cooled to –10° C., and stirred for about 40 minutes at the same temperature. The obtained solid is filtered, washed with precooled hexane (100 mL), and dried at 26° C. to give 37.0 g of the title compound.

Example 3

Preparation of 1-(3-nitropropyl)-4-octylbenzene (Formula VII)

3-Nitro-1-(4-octylphenyl)propan-1-one (37 g) and dichloromethane (185 mL) are charged into a round bottom flask at 25-30° C. and stirred. Triethylsilane (36.87 g) is charged into the flask and the reaction mixture is cooled to 0-5° C. Titanium tetrachloride (28.9 g) in dichloromethane (185 mL) is added to the reaction mixture over the period of 30 minutes at temperature below 5° C. and the reaction mixtures is stirred at a temperature of 25-30° C. for about 1 hour. The reaction mixture is added to water (370 mL) precooled to 0-5° C., stirred, and the organic layer is separated. The organic layer is washed with aq. sodium bicarbonate (2×370 mL), followed by water (370 mL), and brine solution (370 mL). The organic layer is dried over sodium sulphate and evaporated under reduced pressure at about 45° C. to give 64.0 g of the title compound.

Example 4

Preparation of 2-nitro-2-(4-octylphenethyl)propane-1,3-diol (Formula VIII)

1-(3-Nitropropyl)-4-octylbenzene (37 g) and methanol (190 mL) are charged into a round bottom flask and stirred at 25-30° C. Paraformaldehyde (37 g) and triethylamine (38.52 g) are charged into the flask and the reaction mixture is heated to a reflux temperature (about 68° C.). The reaction mixture is maintained at the same temperature for about 2 hours and is cooled to a temperature of 25-30° C. The reaction mixture is evaporated under reduced pressure at a temperature of about 45° C. to obtain crude compound. Water (190 mL) and ethyl acetate (190 mL) are charged to the crude compound, stirred, and the organic layer is separated. The aqueous layer is extracted with ethyl acetate (190 mL) and the organic layer is combined with the initial organic layer. The combined organic layer is washed with water (190 mL) followed by brine solution (190 mL), dried over sodium sulphate, and evaporated under reduced pressure. Hexane (370 mL) is charged at 28° C. and the reaction mass is stirred at the same temperature for about 1 hour. The solid obtained is collected by filtration, washed with hexane (37 mL), and dried at 28° C. for about 3 hours to give 20.5 g of the title compound.

Example 5

Preparation of 2-amino-2-(4-octylphenethyl)propane-1,3-diol hydrochloride (Formula I)

2-Nitro-2-(4-octylphenethyl)propane-1,3-diol (5 g) and methanol (100 mL) are charged into a hydrogenation vessel and stirred at 25-30° C. 10% Pd/C (50% wet, 1 g) is charged into the vessel, a hydrogen pressure of 5 Kg/cm$^2$ applied, and the reaction mixture is stirred at 25-30° C. for about 4 hours. The reaction mixture is filtered through a hyflow bed and washed with methanol (10 mL). The filtrate is charged into a round bottom flask and ether hydrochloric acid (25 mL) is added to adjust the pH of the reaction mixture to 3. The reaction mixture is evaporated under reduced pressure at about 45° C. to obtain 15-20 mL of the concentrated mass. The reaction mass is cooled to 0° C. and ethyl acetate (50 mL) is added over a period of 15 minutes. The reaction mixture is maintained at 0-5° C. for about 1 hour and filtered. The collected solid is washed with precooled ethyl acetate (10 mL) and dried at about 26° C. for 3 hours to give 2.8 g of the title compound.

Example 6

Preparation of
3-nitro-1-(4-octylphenyl)propan-1-one (Formula VI)

Octanophenone (250 g) and dichloromethane (1250 mL) are charged into a round bottom flask at 25-30° C. and stirred. The mixture is cooled to −10° C. to −5° C. and triethylsilane (327.9 g) is added. A solution of titanium tetrachloride (244.1 g) in dichloromethane (1250 mL) is added over a period of 15 minutes and the obtained reaction mixture is maintained at 0-5° C. for 3 hours. The reaction mixture is filtered through a hyflo bed, washed with dichloromethane (500 mL) and the filtrate obtained is charged into a second round bottom flask. The reaction mass (filtrate) is cooled to −10° C. to −5° C. and aluminium chloride (213.2 g) is slowly added to the reaction mass over a period of 15 minutes. A solution of 3-chloropropionyl chloride (173.5 g) in dichloromethane (500 mL) is added over a period of 15 minutes and the obtained reaction mixture is maintained at −10° C. to −5° C. for 3 hours. Water (2500 mL) precooled to 0-10° C. is slowly added at the same temperature and the reaction mixture is stirred for about 1 hour at a temperature of 25-30° C. The organic layer is separated, washed with 5% sodium bicarbonate solution (1250 mL), followed by 20% brine solution (1250 mL) and the organic layer is concentrated under vacuum at 45° C. to obtain crude product (751 g). The crude product obtained and dimethyl formamide (1500 mL) are charged into a round bottom flask at 25-35° C. and stirred. Sodium nitrite (135.5 g) is added and reaction mixture is maintained at 30-35° C. for 3 hour. Water (2500 mL) and ethyl acetate (2500 mL) are added to the reaction mixture, stirred for 30 minutes. The organic layer is separated and the aqueous layer is extracted with ethyl acetate (500 mL). The organic layers are combined, washed with 5% brine solution (2×2500 mL) and concentrated under reduced pressure at 45° C. Hexane (500 mL) is added to the obtained compound and evaporated under reduced pressure at 45° C. to give the title compound.

Yield: 502 g
Purity by HPLC: 94.26%

Example 7

Purification of
3-nitro-1-(4-octylphenyl)propan-1-one (Formula VI)

3-nitro-1-(4-octylphenyl) propan-1-one crude (16.5 g, Purity: 94.26%) and n-hexane (32 mL) are charged into a round bottom flask at 25-30° C. The reaction mixture is cooled to −15 to −10° C., maintained at the same temperature for about 60 minutes and filtered. The obtained wet compound and methanol (48 mL) are charged into a round bottom flask at 25-30° C. and stirred to obtain a clear solution. The solution is cooled to −15 to −10° C. and maintained at the same temperature for about 60 minutes. The obtained solid is filtered, washed with methanol (8 mL) precooled to −5° C. to 0° C. and dried under vacuum at 35-40° C. to give the title compound.

Yield: 8.8 g
Purity by HPLC: 99.5%

Example 8

Preparation of
2-nitro-2-(4-octylphenethyl)propane-1,3-diol
(Formula VIII)

3-nitro-1-(4-octylphenyl)propan-1-one (20 g) and dichloromethane (100 mL) are charged into a round bottom flask at 25-30° C. and stirred. The mixture is cooled to −10° C. to 0° C. and triethylsilane (19.9 g) is added. A solution of titanium tetrachloride (19.57 g) in dichloromethane (100 mL) is added over a period of 15 minutes and the obtained reaction mixture is maintained at −10 to 0° C. for 5 hours. Water (200 mL) precooled to 0-10° C. is slowly added to the reaction mixture over a period of 20 minutes and the temperature is allowed to raise to 25-30° C. The reaction mixture is stirred for about 1 hour, organic layer is separated, washed with 5% sodium bicarbonate solution (100 mL), followed by 20% brine solution (100 mL), the organic layer is concentrated under vacuum at 45° C. to obtain 38.2 g of crude 1-(3-nitropropyl)-4-octylbenzene. Toluene (200 mL) and crude 1-(3-nitropropyl)-4-octylbenzene (38.2 g) are charged into the round bottom flask at 25-30° C. and stirred. Potassium carbonate (18.96 g) and paraformaldehyde (7.21 g) are charged and the reaction mixture is stirred at the same temperature for about 6 hours. The reaction mixture is filtered and washed with toluene (40 mL). The obtained filtrate, water (200 mL) and ethyl acetate (60 mL) are charged into a round bottom flask and stirred for 2 hours. The organic layer is separated, washed with 5% hydrochloric acid solution (100 mL), 5% sodium bicarbonate solution (100 mL) and followed by 5% brine solution (100 mL). The resultant organic layer is concentrated under vacuum at below 45° C. n-Hexane (100 mL) is added to the obtained compound and stirred. The obtained mixture is cooled to 0 to 5° C., maintained at the same temperature for about 60 minutes, filtered and washed with n-hexane (20 mL). The obtained wet compound and toluene (80 mL) are charged into a round bottom flask, heated to 40-45° C. and maintained at the same temperature for about 15 minutes. The reaction mixture is cooled to 0-5° C., maintained for about 45 minutes, filtered and washed the product with toluene (40 mL) precooled to 0-5° C. and the product obtained is dried under vacuum at 25-30° C. to give the title compound.

Yield: 19 g
Purity by HPLC: 99.74%,
Impurity 1: <0.1%

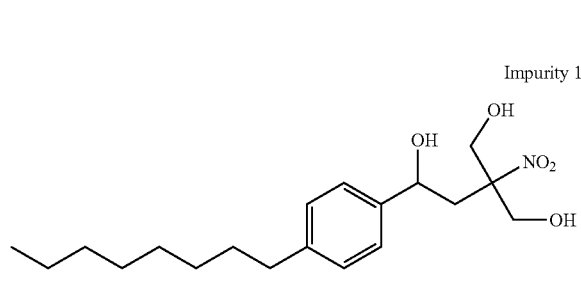 [SMILES: CCCCCCCCc1ccc(C(O)CC(CO)(CO)[N+](=O)[O-])cc1]

Impurity 1

Impurity 2: <0.1%

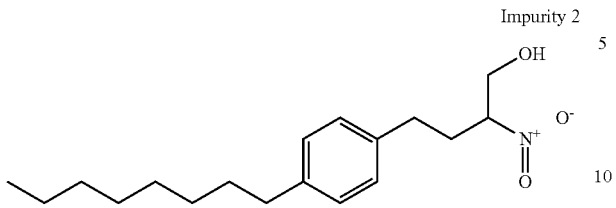

Impurity 2

Impurity 3: <0.1%

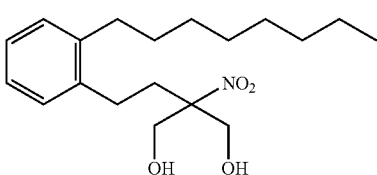

Impurity 3

Impurity 4: <0.1%

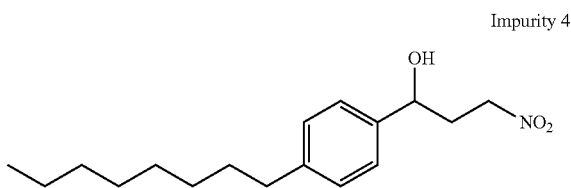 [SMILES: CCCCCCCCc1ccc(C(O)CC[N+](=O)[O-])cc1]

Impurity 4

Example 9

Preparation of
2-amino-2-(4-octylphenethyl)propane-1,3-diol
hydrochloride (Formula I)

2-nitro-2-(4-octylphenethyl)propane-1,3-diol (40 g) and methanol (600 mL) are charged into a hydrogenation vessel at 25 to 30° C. and stirred. 10% Pd/C (14 g) is charged into the vessel, a hydrogen pressure of 4-5 Kg/cm$^2$ applied and the reaction mixture is maintained under the same conditions for about 6 hours. The reaction mixture is filtered through a hyflo bed and washed with methanol (80 mL). The obtained filtrate is charged into a round bottom flask, methanolic hydrochloric acid (47.3 mL) is added and the reaction mass is stirred at 25-30° C. for 10 minutes. The reaction mass is concentrated under reduced pressure at a temperature below 45° C. to obtain 104 mL of the concentrated solution. Ethyl acetate (600 mL) is added to the above concentrated solution, cooled to −5 to 0° C. and maintained at the same temperature for about 1 hour. The solid obtained is filtered, washed with ethyl acetate (80 mL) precooled to 0-5° C. and suction dried. The wet compound and methanol (80 mL) are charged into a round bottom flask at 25-30° C. and stirred to obtain clear solution. Ethyl acetate (80 mL) is added to the above solution, stirred for 10 minutes and filtered through hyflo bed to remove undissovled particles. The bed is washed with mixture of methanol (40 mL) and ethyl acetate (80 mL). The obtained filtrate and ethylacetate (440 mL) are charged into a round bottom flask, cooled to 0-5° C. and maintained at the same temperature for about 60 minutes. The solid obtained is filtered, washed with ethylacetate (80 mL) and dried under vacuum at 25-30° C. to give crystalline compound.

Yield: 26.0 g

Purity by HPLC: 99.9%, Impurity A: 0.01%, Impurity B: not detected, Impurity C: not detected, Impurity D: 0.02%, Impurity E: not detected, Impurity F: 0.02%, Impurity G: 0.02%, Impurity H: not detected, Impurity I: not detected.

Example 10

Preparation of
2-amino-2-(4-octylphenethyl)propane-1,3-diol
(Fingolimod Freebase)

2-nitro-2-(4-octylphenethyl)propane-1,3-diol (3 g) and methanol (60 mL) are charged into a hydrogenation vessel at 25-30° C. and stirred. 10% Pd/C (0.6 g) is charged into the vessel, a hydrogen pressure of 4-5 Kg/cm$^2$ applied and the reaction mixture is maintained under the same conditions for about 5 hours. The reaction mixture is filtered through a hyflow bed and washed with methanol (10 mL). The obtained filtrate is concentrated under reduced pressure at a temperature below 36° C. to obtain 8 mL of concentrated reaction mass. n-Hexane (50 mL) is added, the reaction mixture is cooled to 0-5° C. and maintained at the same temperature for about 1 hour. The solid obtained is filtered, washed with n-hexane (10 mL) and dried under vacuum at 36° C. to give the title compound.

Yield: 2.0 g
Purity by HPLC: 99.1%
XRPD pattern: FIG. 1.

Example 11

Preparation of Amorphous Fingolimod
Hydrochloride

Fingolimod hydrochloride (0.5 g), povidone K-30 (0.5 g), and water (70 mL) are charged into a glass beaker at 28° C. and stirred to form a solution. The solution is filtered, charged to the buchi flask of the freeze drier, cooled to −45° C., and subjected to freeze drying under reduced pressure at 0.1 Torr vacuum, to afford 0.8 g of the product. PXRD pattern: FIG. 2.

Example 12

Preparation of Amorphous Fingolimod
Hydrochloride

Fingolimod hydrochloride (1.5 g), povidone K-30 (1.5 g), and methanol (90 mL) are charged into a round bottom flask at 28° C. and stirred to form a solution. The solution is filtered and the filtrate is evaporated by spray drying, using a Büchi® MINI Spray Dryer B-290 with Büchi® Inert Loop B-295, to afford 1.3 g of the product. PXRD pattern: FIG. 3.

Parameters for the Spray Drier of the Above Experiment:
Aspirator: 70%.
Feed rate: 10%.
N$_2$ pressure: 6-6.5 Kgf/cm$^2$.
Inlet temperature: 70° C.

Example 13

Preparation of Amorphous Fingolimod
Hydrochloride

Fingolimod hydrochloride (1.0 g), povidone K-30 (1.0 g) and demineralized water (125 mL) are charged into a conical flask at 30° C. and stirred to form a solution. The solution is filtered and the filtrate is evaporated by spray drying, using a Büchi® MINI Spray Dryer B-290 with Büchi® Inert Loop B-295, to afford 0.95 g of the product. PXRD pattern: FIG. 4.

Parameters for the Spray Drier of the Above Experiment:
Aspirator: 70%.
Feed rate: 10%.
$N_2$ pressure: 5.0 Kgf/cm$^2$.
Inlet temperature: 110° C.

Example 14

Preparation of 4-Octanoylphenethyl Acetate

Aluminum chloride (32.26 g) and 1,2-dichloroethane (160 mL) are charged into a round bottom flask equipped with a guard tube and addition funnel, stirred for 30 minutes, and cooled to 0° C. A mixture of phenyl acetate (19.417 mL) and octanoyl chloride (24.66 mL) in 1,2-dichloroethane (120 mL) is added over 20 minutes and stirred overnight at room temperature. The mass is cooled to 0° C. and the reaction is quenched with water (400 mL). The mass is extracted with dichloromethane (3×300 mL) and the combined organic layer is washed with brine solution (2×500 mL), followed by drying the organic layer with sodium sulphate and concentrating under vacuum to give crude as yellow color liquid. The crude is purified by silica gel column using 5% ethyl acetate in hexane as the eluent, to give the title compound. Yield: 21.7 g.

Example 15

Preparation of 4-Octylphenethyl Acetate

4-Octanoylphenethyl acetate (17.6 g) and trifluoroacetic acid (31 mL) are charged into a 250 mL single neck round bottom flask equipped with a guard tube and stirred for a few minutes. Triethylsilane (25.7 mL) is added and the mixture is stirred overnight at room temperature. The mixture is poured onto crushed ice and then extracted with ethyl acetate (3×100 mL). The organic layer is washed with sodium bicarbonate (200 mL), then with brine solution, dried with sodium sulphate, and concentrated under vacuum to give crude as brown color liquid. The crude is purified by silica gel column using hexane as the eluent to give the title compound. Yield 10 g Example 16

Preparation of 2-(4-octylphenyl)ethanol

Sodium methoxide (22.6 g) and methanol (450 mL) are charged into a 1 liter single neck round bottom flask equipped with a guard tube and stirred for few minutes to form a clear solution. A mixture of 4-octylphenethyl acetate (58 g) and methanol (50 mL) is added and the mass is stirred for 3 hours at room temperature. Methanol is evaporated and the residue is diluted with water (300 mL) and extracted with ethyl acetate (2×300 mL). The extracts are combined, dried with sodium sulphate and concentrated under vacuum to give crude as yellow color liquid. The crude is purified is by a silica gel column using 30% ethyl acetate/hexane as the eluent to yield the title compound. Yield: 56 g.

Example 17

Preparation of 4-octylphenethyl methanesulfonate 2-(4-Octylphenyl)ethanol (53 g) and dichloromethane (500 mL) are charged into a 1 liter three-neck round bottom flask equipped with guard tube and addition funnel. Triethylamine (83.5 g) is added, the mixture is stirred for 30 minutes, then it is cooled to 0° C. Methanesulphonyl chloride (35.2 mL) is added drop-wise at 0° C. and the mass is stirred for 3 hours at room temperature. The mass is diluted with water (700 mL) and the organic layer is separated and the aqueous layer is extracted with dichloromethane (2×250 mL). The combined organic layers is washed with saturated sodium bicarbonate (500 mL) and brine solution (500 mL). The organic layer is separated, dried with sodium sulphate, and concentrated under vacuum to obtain the title compound. Yield: 70 g.

Example 18

Preparation of 1-(2-iodoethyl)-4-octylbenzene

4-Octylphenethylmethane sulfonate (70 g) and dry tetrahydrofuran (500 mL) are charged into a 1 liter single-neck round bottom flask, equipped with a calcium chloride guard tube and shielded with light protecting black cover. The mixture is stirred for 10 minutes, then sodium iodide (133 g) is added and the mixture is stirred overnight at room temperature. The solvent is evaporated under vacuum and the residue is dissolved in water (300 mL) and extracted with ethyl acetate (2×250 mL). Ethyl acetate extracts are combined, washed with aqueous sodium thiosulphate, dried with sodium sulphate, and concentrated under vacuum to give the title compound. Yield: 70 g.

Example 19

Preparation of diethyl 2-acetamido-2-(4-octylphenethyl) malonate

Cesium carbonate (82.2 g), diethyl 2-acetamidomalonate (77.3 g) and dimethylsulphoxide (300 mL) are charged into a 1 liter single-neck round bottom flask, equipped with a condenser and nitrogen balloon. The mixture is heated to 60° C. and stirred for 3 hours. 1-(2-iodoethyl)-4-octylbenzene (35 g) is added at 60° C. and the mass is stirred overnight at 80° C. The mass is cooled to room temperature, quenched with water (400 mL), and extracted with ethyl acetate (3×250 mL). The ethyl acetate extracts are combined, washed with brine solution (500 mL), dried with sodium sulphate, and concentrated under vacuum to give a crude compound as a solid. The crude is purified by a silica gel column using 15% ethyl acetate/hexane as the eluent to give the title compound. Yield: 65.8 g.

Example 20

Preparation of N-(1-hydroxy-2-(hydroxymethyl)-4-(4-octylphenyl) butan-2-yl) acetamide Sodium borohydride (34.49 g) and dry methanol (450 mL) are charged into a 1 liter three-neck round bottom flask equipped with a guard tube and two condensers, and the mixture is stirred for 20 minutes. Diethyl 2-acetamido-2-(4-octylphenethyl) malonate (65.8 g) is diluted with dry methanol (50 mL) and then added drop-wise until half of the solution is added, and the addition is stopped for 1 hour. Addition is then completed drop-wise over 30 minutes and the mass is maintained overnight at room temperature. The solvent is evaporated under vacuum, and the mass is diluted with water (300 mL) and extracted with ethyl acetate (3×200 mL). The combined organic layer is dried with sodium sulphate, concentrated under vacuum to give the crude mass. The crude is purified by silica gel column using ethyl acetate as the eluent to give the title compound. Yield: 23.5 g.

Example 21

Preparation of Fingolimod Hydrochloride

N-(1-Hydroxy-2-(hydroxymethyl)-4-(4-octylphenyl)butan-2-yl) acetamide (23.5 g) is charged into a 250 mL single-neck round bottom flask equipped with a condenser and 3N hydrochloric acid (100 mL) is added. The mixture is heated to 100° C. and stirred for 3 hours. The mass is cooled to room temperature and maintained overnight. The mass is extracted with ethyl acetate (3×100 mL) and the ethyl acetate extracts are combined, dried with sodium sulphate, and concentrated under vacuum to produce a gummy solid. Ethanolic hydrochloride solution is added to the solid, stirred for 3 hours at room temperature and the obtained solid is separated by filtration and suction dried. The solid is recrystallized from an isopropyl alcohol solution to give fingolimod hydrochloride. Yield: 5.7 g.

Example 22

Preparation of 3-nitro-1-(4-octylphenyl)propan-1-one

3-Chloro-1-(4-octylphenyl)propan-1-one (110 g) and acetone (1 L) are charged into a round bottom flask equipped with a condenser and guard tube and stirred. Sodium nitrite (271 g) is added and the mixture is slowly heated to 80° C. and maintained at that temperature for about 21 hours. The mass is cooled to 58° C., sodium nitrite (10 g) is added, and the mass is maintained at 78° C. for about 6 hours. The solvent is evaporated under reduced pressure. The compound obtained is diluted with water (250 mL) and extracted with ethyl acetate (2×500 mL). The combined organic layer is dried over anhydrous sodium sulphate (50 g) and concentrated under reduced pressure to give solid. Hexane (500 mL) is added and the mixture is cooled to −10° C. and stirred for 20 minutes. The formed solid is separated by filtration and washed with cold hexane (2×100 mL) to obtain the title compound as an off-white solid. Yield: 75 g.

Example 23

Preparation of 3-nitro-1-(4-octylphenyl)propan-1-ol

3-Nitro-1-(4-octylphenyl)propan-1-one (75 g) and methanol (750 mL) are charged into a round bottom flask equipped with a condenser and guard tube, stirred to 10 minutes and the mixture is cooled to 6° C. Sodium borohydride (20.2 g) is added in portions over 30 minutes. Allowed the mixture to room temperature, stirred for 3 hours and solvent is removed under reduced pressure to obtain a solid. The solid is diluted with water (1000 mL), ethyl acetate (1000 mL) is added, the separated solid is filtered. The solid, ethyl acetate (200 mL), and water (200 mL) are charged in a round bottom flask and stirred at room temperature, and 6N HCl (100 mL) is added drop-wise. The organic layer is separated, washed with water (200 mL), dried over sodium sulphate, and concentrated under reduced pressure to give the title compound as a yellow liquid. Yield: 30 g.

Example 24

Preparation of 1-(3-nitropropyl)-4-octylbenzene

3-Nitro-1-(4-octylphenyl)propan-1-ol (30 g) and trifluoroacetic acid (47 mL) are charged into a round bottom flask equipped with a calcium chloride guard tube. The mixture is cooled to 0° C., triethylsilane (32.5 mL) is added, and the mixture is stirred overnight at room temperature. The mass is poured onto crushed ice (200 g) and the mixture is extracted with ethyl acetate (2×200 mL). The combined organic layer is dried over sodium sulphate and concentrated under reduced pressure, to give the crude as a color liquid. The crude obtained is purified by silica gel column chromatography (100-200 mesh, 500 g) using 5% ethyl acetate in hexane as the eluent, and the eluted fraction containing the desired compound are pooled, evaporated under reduced pressure to give the title compound. Yield: 19.8 g.

Example 25

Preparation of 2-nitro-2-(4-octylphenethyl)propane-1,3-diol 1-(3-nitropropyl)-4-octylbenzene (43 g) and absolute ethanol (400 mL) are charged into a round bottom flask equipped with a condenser and calcium guard tube. Paraformaldehyde (43 g) and triethylamine (64.8 mL) are added. The mixture is heated to 70° C., stirred for 3 hours, and is concentrated under reduced pressure at 50° C. to obtain a solid. The solid is dissolved in ethyl acetate (300 mL), the solution is washed with cold water (2×200 mL), and the organic layer is dried over anhydrous sodium sulphate. The organic layer is concentrated under reduced pressure to obtain a yellow solid. Hexane (500 mL) is added and the mixture is cooled to −20° C. and stirred for 20 minutes. The formed solid is separated by filtration and washed with cold hexane (2×100 mL) to obtain the title compound as an off-white solid. Yield: 26 g.

Example 26

Preparation of 2-amino-2-(4-octylphenethyl)propane-1,3-diol

2-Nitro-2-(4-octylphenethyl)propane-1,3-diol (25 g), absolute ethanol (250 mL) and 10% Pd on carbon (5 g, 50% wet) are charged into a 500 mL steel hydrogenation flask under a $N_2$ atmosphere and the flask is equipped with a para shaker hydrogen operator. The mixture is hydrogenated with a $H_2$ pressure of 60 psi (415 kPa) at room temperature for 2 hours and filtered through a Celite bed and washed with ethylacetate (200 mL). The filtrate is concentrated under reduced pressure at 50° C. to give the title compound as a white solid. Yield: 16 g.

The invention claimed is:

1. A process for the preparation of fingolimod of formula (Ia)

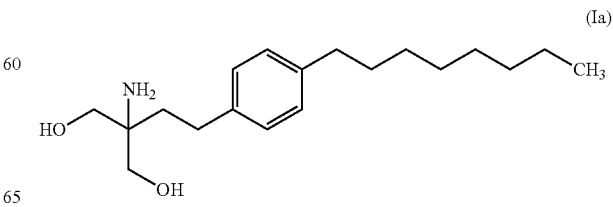

or its salt comprising:

a) reducing 3-nitro-1-(4-octylphenyl)propan-1-one of formula (VI):

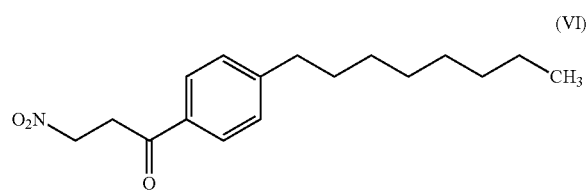 [SMILES: CCCCCCCCc1ccc(C(=O)CC[N+](=O)[O-])cc1]

(VI)

using a Lewis acid and a trialkyl silane to obtain a compound of formula (VII); and

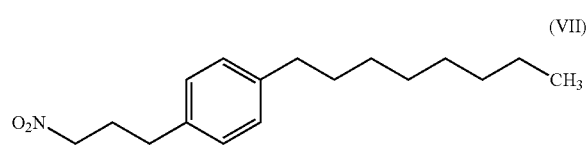 [SMILES: CCCCCCCCc1ccc(CCC[N+](=O)[O-])cc1]

(VII)

b) reacting the compound of formula (VII):

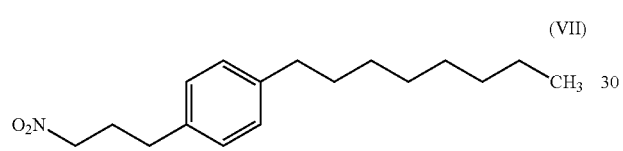

(VII)

with paraformaldehyde to obtain a compound of formula (VIII); and

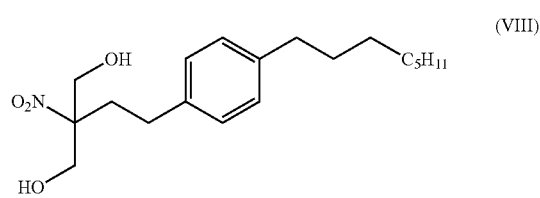

(VIII)

c) reacting the compound of formula (VIII) with a reducing agent to obtain fingolimod of formula (1a):

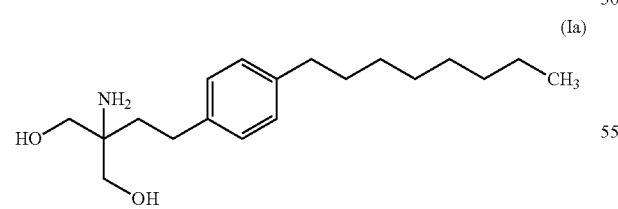

(Ia)

or its salt.

2. The process of claim 1, wherein the salt of formula (Ia) is a hydrochloride salt.

3. The process of claim 1, wherein the Lewis acid used in step a) is selected from $TiCl_4$, $AlCl_3$, or $BF_3$.

4. The process of claim 1, wherein the trialkylsilanes used in step a) are selected from triethylsilane, trimethylsilane, or triisopropyl silane.

5. The process of claim 1, wherein step a) is carried out in the presence of a halogenated hydrocarbon solvent, a hydrocarbon solvent or from mixtures thereof.

6. The process of claim 1, wherein step b) is carried out in the presence of a base selected from an organic base such as diethylamine, triethylamine, n-butylamine, propylamine, diisopropylethylamine, dicyclohexylamine or an inorganic base such as sodium carbonate, potassium carbonate.

7. The process of claim 1, wherein step b) is carried out in the presence of an alcohol such as methanol, ethanol, polar aprotic solvents such as dimethylformamide, dimethyl sulfoxide, tetrahydrofuran, acetone, acetonitrile, and aromatic solvents such as toluene, xylene or mixtures thereof.

8. The process of claim 1, wherein the reducing agent used in step a) is selected from sodium borohydride, lithium borohydride, lithium aluminium hydride, Pd on carbon, Raney® nickel, or $Pd(OH)_2$, under a hydrogen atmosphere.

9. The process of claim 1, wherein step c) is carried out in the presence of an alcohol selected from methanol, ethanol, a polar aprotic solvent selected from dimethylformamide, dimethyl sulfoxide, tetrahydrofuran, acetone, acetonitrile, or an aromatic solvent selected from toluene, xylene, or mixtures thereof.

10. A process for the preparation of fingolimod of formula (Ia)

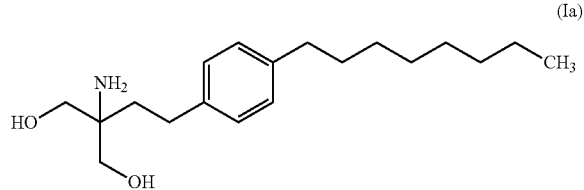 [SMILES: CCCCCCCCc1ccc(CCC(N)(CO)CO)cc1]

(Ia)

or its salt comprising:

a. reacting the compound of formula (VII):

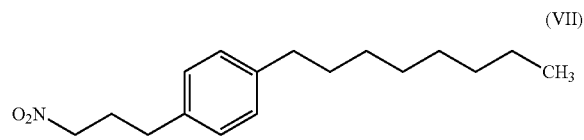 [SMILES: CCCCCCCCc1ccc(CCC[N+](=O)[O-])cc1]

(VII)

with paraformaldehyde to obtain a compound of formula (VIII); and

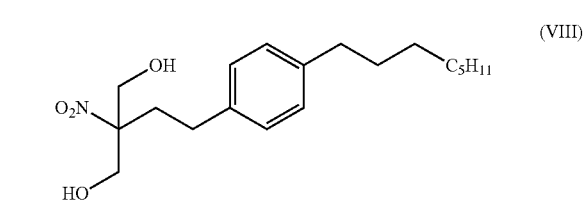

(VIII)

b. reacting the compound of formula (VIII) with a reducing agent to obtain fingolimod of formula (I a):

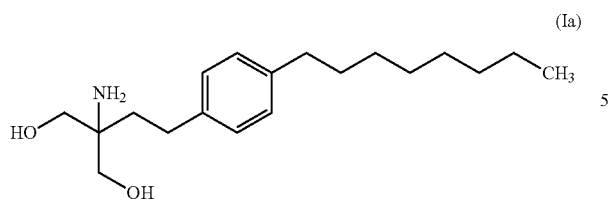

(Ia)

or its salt.

11. The process of claim 10, wherein the base used in step a) is selected from an organic base such as diethylamine, triethylamine, n-butylamine, propylamine, diisopropylethylamine, dicyclohexyiamine or an inorganic base such as sodium carbonate, potassium carbonate.

12. The process of claim 10, wherein the reducing agent of step b) is selected from sodium borohydride, lithium borohydride, lithium aluminium hydride, Pd on carbon, Raney® nickel, or $Pd(OH)_2$, under a hydrogen atmosphere.

13. The process of claim 1, further comprises the purification of fingolimod hydrochloride, wherein the purification comprises:
   a. providing a solution of fingolimod hydrochloride in methanol or methanol and ethyl acetate mixture;
   b. optionally adding ethyl acetate;
   c. cooling the solution to a temperature below 10° C.;
   d. isolating fingofimod hydrochloride.

14. The process of claim 13, wherein the isolated fingolimod hydrochloride is crystalline.

* * * * *